(12) United States Patent
Hanein et al.

(10) Patent No.: US 11,567,028 B2
(45) Date of Patent: Jan. 31, 2023

(54) SENSING ELECTRODE AND METHOD OF FABRICATING THE SAME

(71) Applicant: Ramot at Tel-Aviv University Ltd., Tel-Aviv (IL)

(72) Inventors: Yael Hanein, Tel-Aviv (IL); Lilach Bareket, Tel-Aviv (IL); Moshe David-Pur, Tel-Aviv (IL); David Rand, Tel-Aviv (IL); Lilah Inzelberg, Tel-Aviv (IL); David Rabinovich, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 140 days.

(21) Appl. No.: 15/779,116

(22) PCT Filed: Nov. 29, 2016

(86) PCT No.: PCT/IL2016/051278
§ 371 (c)(1),
(2) Date: May 25, 2018

(87) PCT Pub. No.: WO2017/090050
PCT Pub. Date: Jun. 1, 2017

(65) Prior Publication Data
US 2018/0321173 A1 Nov. 8, 2018

Related U.S. Application Data

(60) Provisional application No. 62/260,563, filed on Nov. 29, 2015.

(51) Int. Cl.
*G01N 27/28* (2006.01)
*A61B 5/282* (2021.01)
(Continued)

(52) U.S. Cl.
CPC ............ *G01N 27/283* (2013.01); *A61B 5/282* (2021.01); *A61B 5/287* (2021.01); *A61B 5/291* (2021.01);
(Continued)

(58) Field of Classification Search
CPC G01N 27/283; A61B 5/04085; A61B 5/0422; A61B 5/0478; A61B 5/0492; A61B 5/0496; A61B 5/4806
See application file for complete search history.

(56) References Cited

U.S. PATENT DOCUMENTS 5,749,365 A * 5/1998 Magill ................ A61B 5/1135
600/484
6,066,093 A 5/2000 Kelly et al.
(Continued)

FOREIGN PATENT DOCUMENTS

| CA | 2938018 | 8/2015 |
|---|---|---|
| CN | 104000574 | 8/2014 |

(Continued)

OTHER PUBLICATIONS

International Preliminary Report on Patentability dated Jun. 7, 2018 From the International Bureau of WIPO Re. Application No. PCT/IL2016/051278. (8 Pages).
(Continued)

*Primary Examiner* — Christopher A Flory

(57) ABSTRACT

A method of measuring signals from a surface. The method comprises: placing on the surface a flexible sensing device having an array of coated electrodes, wherein at least one electrode of the array is metallic and is at least partially coated by a polymer; and collecting signals from the sensing device.

9 Claims, 19 Drawing Sheets

(51) Int. Cl.
| | | |
|---|---|---|
| *A61B 5/287* | (2021.01) | |
| *A61B 5/291* | (2021.01) | |
| *A61B 5/296* | (2021.01) | |
| *A61B 5/398* | (2021.01) | |
| *A61B 5/00* | (2006.01) | |
| *G01N 27/30* | (2006.01) | |

(52) U.S. Cl.
CPC .............. *A61B 5/296* (2021.01); *A61B 5/398* (2021.01); *A61B 5/4806* (2013.01); *G01N 27/308* (2013.01); *A61B 2562/0215* (2017.08); *A61B 2562/043* (2013.01); *A61B 2562/125* (2013.01)

(56) References Cited

U.S. PATENT DOCUMENTS

| | | | | |
|---|---|---|---|---|
| 6,503,381 | B1* | 1/2003 | Gotoh | G01N 27/3272 204/403.01 |
| 6,687,523 | B1* | 2/2004 | Jayaramen | A41D 13/1281 600/388 |
| 7,206,630 | B1* | 4/2007 | Tarler | A61B 5/0006 600/509 |
| 7,559,902 | B2* | 7/2009 | Ting | A61B 5/0408 600/529 |
| 9,149,229 | B1* | 10/2015 | Tarler | A61B 5/0006 |
| 9,192,933 | B2* | 11/2015 | Whitesides | G01N 27/3272 |
| 9,693,732 | B1* | 7/2017 | Tarler | A61B 5/0006 |
| 2002/0095080 | A1* | 7/2002 | Cory | A61B 5/0531 600/393 |
| 2004/0138546 | A1* | 7/2004 | Reho | A61B 5/6831 600/382 |
| 2006/0064035 | A1* | 3/2006 | Wang | A61B 5/1486 600/583 |
| 2006/0253078 | A1* | 11/2006 | Wu | A61M 37/0015 604/173 |
| 2007/0060815 | A1* | 3/2007 | Martin | A61B 5/0408 600/372 |
| 2007/0060862 | A1* | 3/2007 | Sun | A61N 1/044 604/20 |
| 2007/0249952 | A1* | 10/2007 | Rubin | A61B 5/4812 600/544 |
| 2008/0127978 | A1* | 6/2008 | Rubin | A61B 5/369 128/204.23 |
| 2008/0146958 | A1* | 6/2008 | Guillory | A61B 5/6814 600/544 |
| 2009/0038820 | A1 | 2/2009 | Keefer | |
| 2009/0088652 | A1* | 4/2009 | Tremblay | A61B 5/6814 600/388 |
| 2009/0280153 | A1* | 11/2009 | Hunter | A61N 1/3956 424/423 |
| 2009/0294803 | A1* | 12/2009 | Nuzzo | H01L 29/04 257/213 |
| 2009/0306485 | A1* | 12/2009 | Bell | A61B 5/04085 600/301 |
| 2010/0198038 | A1* | 8/2010 | Nagata | A61B 5/04085 600/372 |
| 2010/0298687 | A1 | 11/2010 | Yoo et al. | |
| 2011/0087315 | A1* | 4/2011 | Richardson-Burns | A61N 1/0536 607/116 |
| 2011/0118581 | A1 | 5/2011 | Jadidi et al. | |
| 2011/0251469 | A1* | 10/2011 | Varadan | A61B 5/0022 600/301 |
| 2011/0260115 | A1* | 10/2011 | Kim | H01B 1/22 252/503 |
| 2012/0209100 | A1* | 8/2012 | De Beeck | A61M 5/14276 600/377 |
| 2012/0226130 | A1* | 9/2012 | De Graff | A61B 18/1492 600/393 |
| 2013/0013028 | A1* | 1/2013 | Kriksunov | A61N 1/36021 607/62 |
| 2013/0041235 | A1* | 2/2013 | Rogers | A61N 1/05 600/306 |
| 2013/0211208 | A1* | 8/2013 | Varadan | A61B 5/6804 600/301 |
| 2013/0281795 | A1* | 10/2013 | Varadan | A61B 5/6804 600/301 |
| 2013/0281815 | A1* | 10/2013 | Varadan | A61B 5/04085 600/388 |
| 2014/0107458 | A1* | 4/2014 | Op de Beeck | A61B 5/291 600/391 |
| 2014/0128703 | A1* | 5/2014 | Simpson | A61B 5/14532 600/347 |
| 2014/0128704 | A1* | 5/2014 | Simpson | A61B 5/7203 600/347 |
| 2014/0200432 | A1* | 7/2014 | Banerji | A63B 21/4017 600/383 |
| 2014/0235991 | A1 | 8/2014 | Gadsby | |
| 2014/0277318 | A1 | 9/2014 | Richardson-Burns et al. | |
| 2014/0303452 | A1* | 10/2014 | Ghaffari | A61B 18/1815 600/301 |
| 2015/0068069 | A1* | 3/2015 | Tran | A43B 13/183 36/136 |
| 2015/0164404 | A1* | 6/2015 | Euliano | A61B 5/7278 600/301 |
| 2015/0238106 | A1* | 8/2015 | Lappalainen | A61B 5/684 600/301 |
| 2015/0297136 | A1* | 10/2015 | Op De Beeck | A61B 5/686 600/300 |
| 2015/0306373 | A1* | 10/2015 | Bouton | A61N 1/36003 607/48 |
| 2015/0335876 | A1* | 11/2015 | Jeffery | A61N 1/0492 607/139 |
| 2015/0351690 | A1* | 12/2015 | Toth | A61B 5/296 600/373 |
| 2015/0370320 | A1* | 12/2015 | Connor | A61B 5/1126 345/173 |
| 2016/0089045 | A1* | 3/2016 | Sadeghian-Motahar | A61B 5/0531 600/386 |
| 2016/0346530 | A1* | 12/2016 | Jeffery | A61N 1/0492 |
| 2017/0035317 | A1* | 2/2017 | Jung | A61B 3/145 |
| 2017/0079543 | A1* | 3/2017 | Sadeghian-Motahar | A61B 5/30 |
| 2017/0188916 | A1* | 7/2017 | Wang | C08L 39/06 |
| 2017/0188922 | A1* | 7/2017 | Lee | A61K 38/28 |
| 2017/0325724 | A1* | 11/2017 | Wang | A61B 5/1486 |
| 2017/0348117 | A1* | 12/2017 | Strbac | A61F 2/72 |
| 2017/0354372 | A1* | 12/2017 | Varadan | A61B 5/0408 |
| 2018/0103917 | A1* | 4/2018 | Kim | A61B 5/24 |
| 2018/0154140 | A1* | 6/2018 | Bouton | A61B 5/389 |

FOREIGN PATENT DOCUMENTS

| | | |
|---|---|---|
| WO | WO 2015/031265 | 3/2015 |
| WO | WO 2017/090050 | 6/2017 |

OTHER PUBLICATIONS

International Search Report and the Written Opinion dated Mar. 7, 2017 From the International Searching Authority Re. Application No. PCT/IL2016/051278. (14 Pages).

Bandodkar et al. "Tattoo-Based Potentiometric Ion-Selective Sensors for Epidermal pH Monitoring", The Analyst, 138(1): 123-128, Oct. 19, 2012.

Bareket et al. "Carbon Nanotubes Based Electrochemical Biosensor for Detection of Formaldehyde Released From A Cancer Cell Line Treated With Formaldehyde-Releasing Anticancer Prodrugs", Bioelectrochemistry, 77(2): 94-99, Available Online Jul. 8, 2009.

Cogan "Neural Stimulation and Recording Electrodes", Annual Review of Biomedical Engineering, 10: 275-309, Published Online Apr. 22, 2008.

Cugnet et al. "A Novel Microelectrode Array Combining Screen-Printing and Femtosecond Laser Ablation Technologies: Development, Characterization and Application to Cadmium Detection", Sensors and Actuators B: Chemical, 143(1): 158-163, Available Online Aug. 31, 2009.

(56) References Cited

OTHER PUBLICATIONS

Dams et al. "Plasma Deposition of Thiophene Derivatives Under Athmospheric Pressure", Chemical Vapor Deposition, 12(12): 719-727, Published Online Dec. 12, 2006.
Gabay et al. "Electro-Chemical and Biological Properties of Carbon Nanotube Based Multi-Electrode Arrays", Nanotechnology, 18(3): 035201-1-035201-6, Jan. 3, 2007.
Gong et al. "Plasma-Polymerized Polyaniline Films: Synthesis and Characterization", Journal of Polymer Science: Part A: Polymer Chemistry, 36(4): 633-643, Mar. 1998.
Huigen et al. "Investigation Into the Origin of the Noise of Surface Electrodes", Medical & Biological Engineering & Computing, 40(3): 332-338, May 2002.
Larsen et al. "Effects of Positive and Negative Affect on Electromyographic Activity Over Zygomaticus Major and Corrugator Supercilii", Psychophysiology, 40(5): 776-785, Sep. 2003.
Li et al. "Recent Developments and Applications of Screen-Printed Electrodes in Environmental Assays—A Review", Analytica Chimica Acta, 734: 31-44, Available Online May 20, 2012.
Loeb et al. "Toward the Ultimate Metal Microelectrode", Journal of Neuroscience Methods, 63(1-2): 175-183, Dec. 1995.
Malzahn et al. "Wearable Electrochemical Sensors for In Situ Analysis in Marine Environments", The Analyst, 136(14): 2912-2917, Published Online Jun. 2, 2011.
Merrill et al. "Electrical Stimulation of Excitable Tissue: Design of Efficacious and Safe Protocols", Journal of Neuroscience Methods, 141(2): 171-198, Feb. 15, 2005.
Mu et al. "A Novel Screen-Printed Electrode Array for Rapid High-Throughput Detection", The Analyst, 137(14): 3220-3223, Published Online May 1, 2012.
Nastase et al. "Effect of P-Toluene Sulphonic Acid Doping on the Properties of Plasma Polymerized Aniline Thin Films", Synthetic Metals, 147(1-3): 133-138, Available Online Oct. 27, 2004.
Robinson "The Electrical Properties of Metal Microelectrodes", Proceedings of the IEEE, 56(6): 1065-1071, Jun. 1968.
Sagle et al. "PEG-Coated Reverse Osmosis Membranes: Desalination Properties and Fouling Resistance", Journal of Membrane Science, 340(1-2): 92-108, Available Online May 18, 2009.
Van Boxtel "Facial EMG as A Tool for Inferring Affective States", Proceedings of Measuring Behavior, Einhoven, The Netherlands, Aug. 24-27, 2010, p. 104-108, Aug. 2010.
Yan et al. "A Disposable Electrochemical Immunosensor Based on Carbon Screen-Printed Electrodes for the Detection of Prostate Specific Antigen", Biosensors and Bioelectronics, 38(1): 355-361, Available Online Jun. 21, 2012.
Zhang "Surface Modification by Plasma Polymerization and Application of Plasma Polymers as Biomaterials", Thesis PhD, Disseration zur Erlangung des Grades Doktor der naturwissenschaften am Fachbereich Chemie und Pharmazie der Johannes Gutenberg-Universität Mainz, Germany, p. 1-127, Dec. 2003.
Zou et al. "Surface Hydrophilic Modification of RO Membranes by Plasma Polymerization for Low Organic Fouling", Journal of Membrane Science, 369(1-2): 420-428, AVailable Online Dec. 17, 2010.
Supplementary European Search Report and the European Search Opinion dated Jun. 12, 2019 From the European Patent Office Re. Application No. 16868156.7. (9 Pages).
Brooks et al. "Plasma Polymerization: A Versatile and Attractive Process for Conformal Coating", Originally Published in the IPC APEX EXPO Conference Proceedings, SMT (Online), XP055591458, p. 38, Retrieved from the Internet, Feb. 1, 2013,.

\* cited by examiner

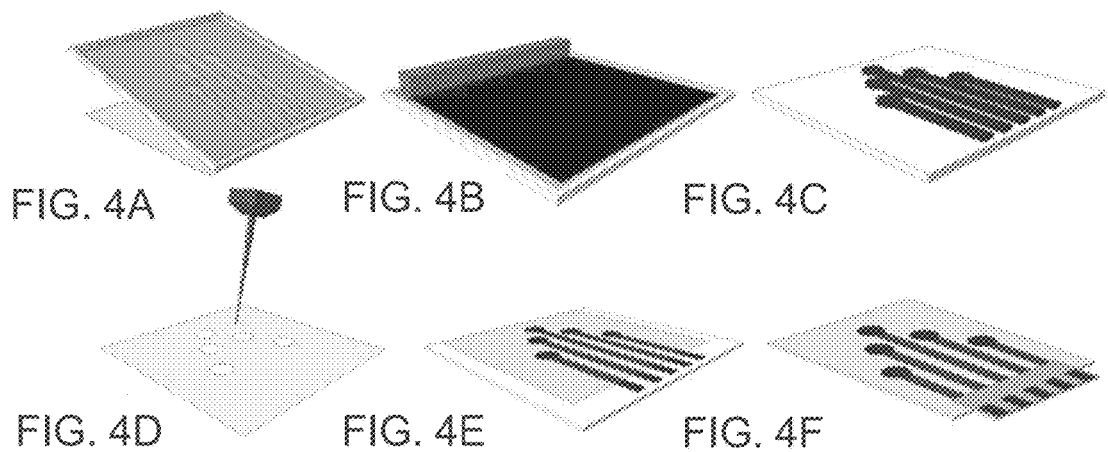
FIG. 4A   FIG. 4B   FIG. 4C
FIG. 4D   FIG. 4E   FIG. 4F
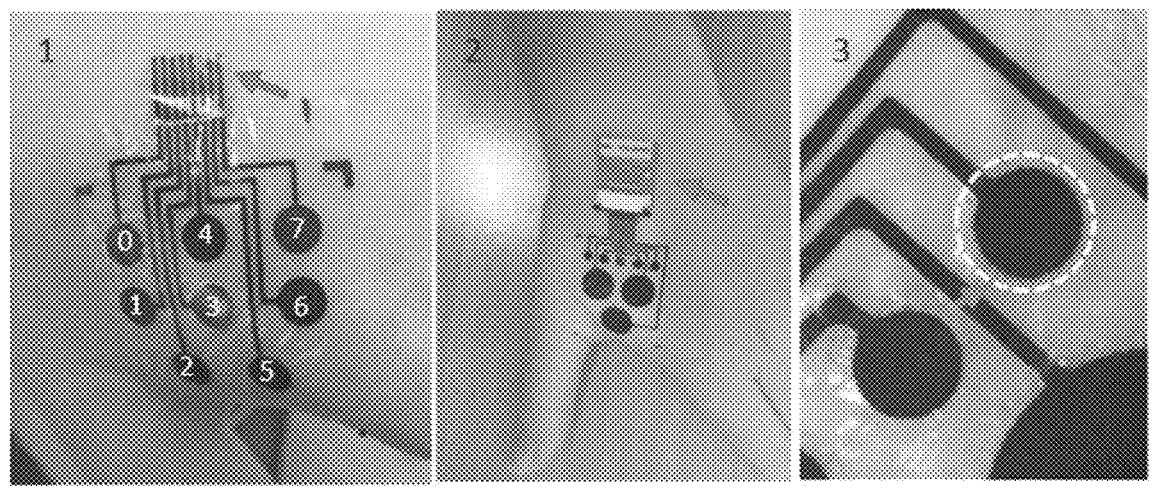
FIG. 5A   FIG. 5B   FIG. 5C FIG. 13A
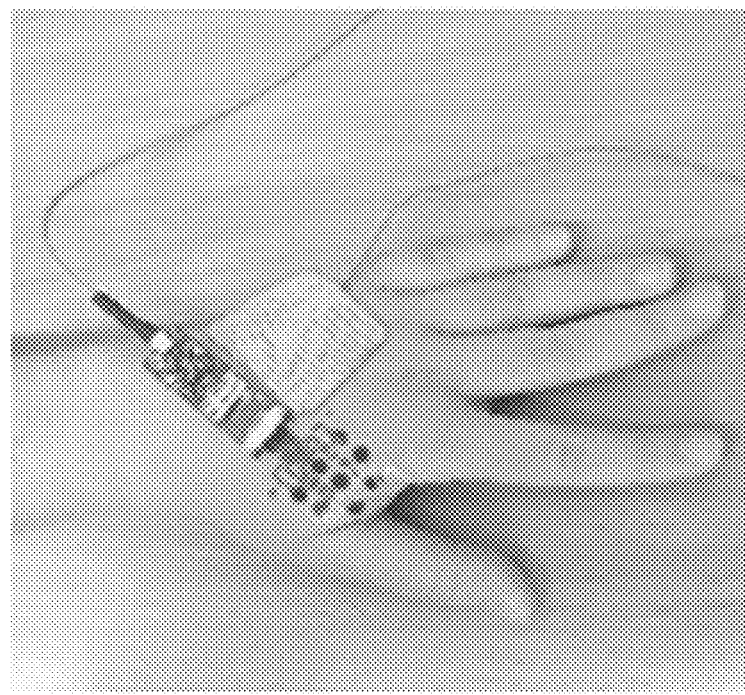
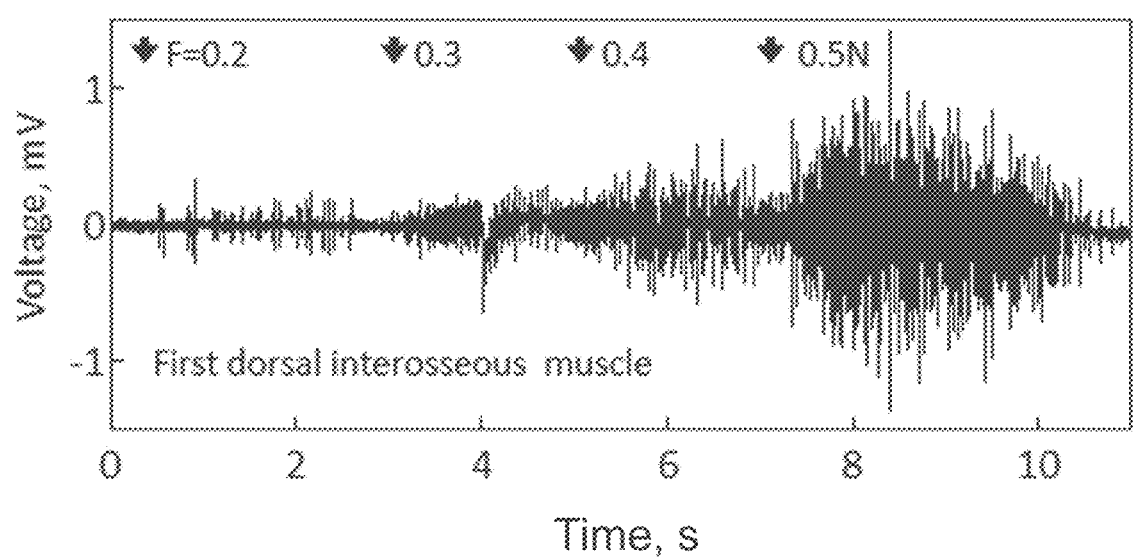
FIG. 13B

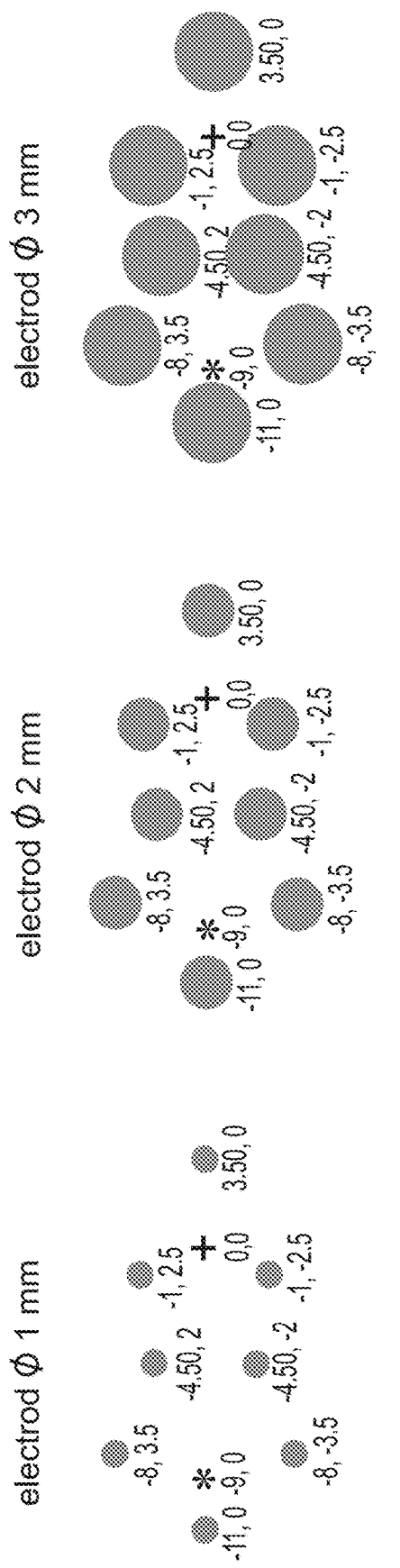
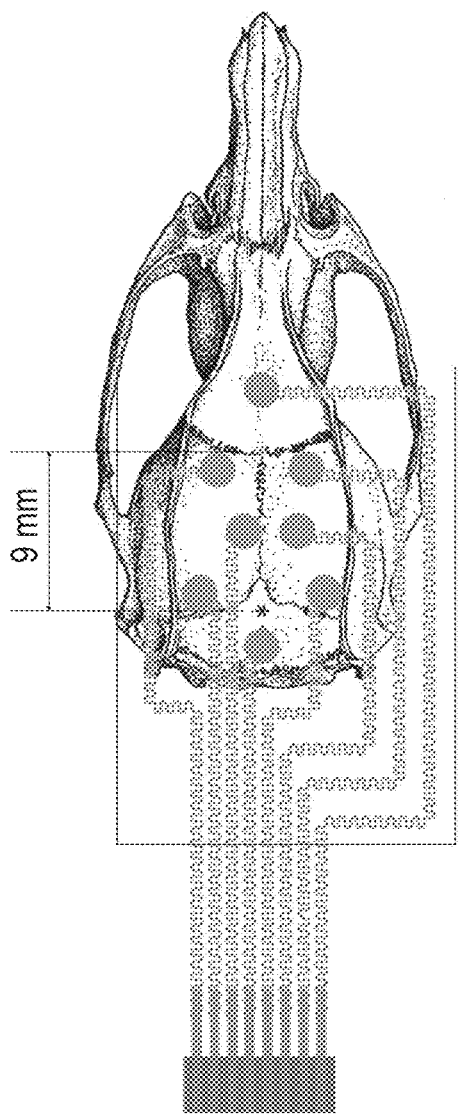
FIG. 15A  FIG. 15B  FIG. 15C  FIG. 15D

SENSING ELECTRODE AND METHOD OF FABRICATING THE SAME

RELATED APPLICATION

This application is a National Phase of PCT Patent Application No. PCT/IL2016/051278 having International filing date of Nov. 29, 2016, which claims the benefit of priority under 35 USC § 119(e) of U.S. Provisional Patent Application No. 62/260,563 filed on Nov. 29, 2015. The contents of the above applications are all incorporated by reference as if fully set forth herein in their entirety.

The work leading to this invention has received funding from the European Research Council under the European Union's Seventh Framework Programme (FP7/2007-2013)/ERC grant agreement no. 306707.

FIELD AND BACKGROUND OF THE INVENTION

The present invention, in some embodiments thereof, relates to sensing of physiological data and, more particularly, but not exclusively, to a sensing electrode and method of fabricating the same.

Skin electrodes are a common noninvasive tool used to record chemical and electrical-activity from the surface of the body. Electrical activity applications include electroencephalography (EEG), electromyography (EMG), electrocardiography (ECG) and Electrooculography (EOG). Surface EMG (sEMG) in particular has been suggested for a very wide range of applications such as brain-machine interfacings and facial sEMG to record emotions [Nicolelis, Nature, 2001, 409, 403-407, O'Doherty, et al., 2011, Nature 479, 228-231, Hardyck et al., 1966, Science 154, 1467-1468, Zajonc, 1985, Science 228, 15-21]. By identifying specific muscle activation during facial expressions, facial sEMG can indeed distinguish between mood states including between a Duchenne (genuine) and a non-Duchenne (fake) smile [Johnson et al., 2010, Cognition & Emotion 24, 299-321]. sEMG recording can be used for quantifying and reporting elementary emotions exceeding the reliability of self-reporting, or image analysis.

Screen printing is a technique that forms a print film comprising ink, paste, or the like on the surface of a material to be printed using a printing plate [see, e.g., U.S. Pat. No. 6,065,398]. Screen-printed electrodes (SPEs) on temporary tattoo film were reported for epidermal pH monitoring [Bandodkar et al., 2013, Analyst 138, 123-128]. Screen-printed disposable electrodes have been used in the field of chemical and biological sensing (Cugnet et al., 2009, Sensors and Actuators, B-Chemical 143(1): 158-163, Malzahn et al., 2011, Analyst 136(14): 2912-2917, Li et al., 2012, Analytica Chimica Acta 734: 31-44, Bareket 2010, Bioelectrochemistry, 77(2): 94-99, Mu et al., 2012, Analyst 137(14): 3220-3223, and Yan et al., 2012, Biosensors & Bioelectronics 38(1): 355-361].

SUMMARY OF THE INVENTION

According to an aspect of some embodiments of the present invention there is provided a method of measuring signals from a surface. The method comprises: placing on the surface a sensing device having an array of dry electrodes, such that there is a direct contact between the electrodes and the surface, and collecting signals from the sensing device.

According to an aspect of some embodiments of the present invention there is provided a method of measuring signals from a surface. The method comprises: placing on the surface a flexible sensing device having an array of coated electrodes, wherein at least one electrode of the array is metallic and is at least partially coated by a polymer; and collecting signals from the sensing device.

According to some embodiments of the invention the collecting is executed continuously or intermittently over a time period of at least a few hours without detaching the sensing device from the surface.

According to some embodiments of the invention the collecting is executed continuously or intermittently over a time period of at least a few hours while a signal to noise ratio of the signals is not reduced by more than 10%.

According to some embodiments of the invention the sensing device comprises a double sided adhesive film, wherein the coated electrodes are attached to one side of aid film and the surface is attached to an opposite side of the film, and wherein the film comprises a plurality of opening to expose a sensing portion of each electrode to the surface.

According to some embodiments of the invention the electrodes are printed electrodes.

According to some embodiments of the invention the signals are EMG signals.

According to some embodiments of the invention the signals are EEG signals.

According to some embodiments of the invention the signals are ECG signals.

According to some embodiments of the invention the signals are EOG signals.

According to an aspect of some embodiments of the present invention there is provided a method of fabricating a sensing device. The method comprises: printing metallic electrodes on a flexible substrate to form an array; and applying plasma coating to the metallic electrodes, to induce polymerization of a monomer to a polymer onto the electrodes, wherein the plasma coating is characterized by a monomer vapor pressure of less than 1 mbar.

According to some embodiments of the invention the plasma coating is characterized by plasma power of 10-100 W.

According to some embodiments of the invention the method comprises attaching the substrate to one side of a double sided adhesive film, and forming a plurality of opening in the film to expose a sensing portion of each electrode at an opposite side of the film.

According to some embodiments of the invention the printing comprises screen printing.

According to some embodiments of the invention the printing comprises inkjet printing.

According to some embodiments of the invention the printing comprises carbon nanotube transfer.

According to some embodiments of the invention the metallic electrode is comprises carbon.

According to some embodiments of the invention the metallic electrode is comprises a metal selected from the group consisting of carbon, silver and silver chloride.

According to some embodiments of the invention the polymer is a plasma polymerized monomer that is selected from the group consisting of a thiophene, a pyrrole, an aniline, and substituted derivatives thereof.

According to some embodiments of the invention the thiophene is 3,4-ethylenedioxythiophene.

According to some embodiments of the invention the surface is a surface of a biological material.

According to some embodiments of the invention the surface is a surface of a natural tissue.

According to some embodiments of the invention the surface is a surface of an ex-vivo natural tissue.

According to some embodiments of the invention the surface is a surface of an in-vivo natural tissue.

According to some embodiments of the invention the surface is a surface of an artificial tissue.

According to some embodiments of the invention the surface is a surface of an ex-vivo artificial tissue.

According to some embodiments of the invention the surface is a surface of an in-vivo artificial tissue.

According to some embodiments of the invention the surface is a skin of a subject.

According to some embodiments of the invention the surface is a surface of an internal organ of a subject.

According to some embodiments of the invention the surface is a surface of a cell culture.

According to some embodiments of the invention the method is employed for sleep analysis.

According to an aspect of some embodiments of the present invention there is provided a sensing device. The device comprises an array of coated electrodes, wherein at least one electrode of the array is metallic and is at least partially coated by a polymer, and wherein the polymer is a plasma polymerized monomer.

According to some embodiments of the invention the device wherein the monomer is selected from the group consisting of a thiophene, a pyrrole, an aniline, and substituted derivatives thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-F are schematic illustrations of a process used for fabricating electrodes in experiments performed according to some embodiments of the present invention;

FIGS. 5A-C are images showing the fabricated array once placed on a hand of a human volunteer in experiments performed according to some embodiments of the present invention;

FIGS. 13A-B show images obtained during functional recordings, performed according to some embodiments of the present invention;

FIGS. 15A-D illustrate layouts of carbon nanotube electrodes, according to various exemplary embodiments of the present invention.

DESCRIPTION OF SPECIFIC EMBODIMENTS OF THE INVENTION

Figure 1:
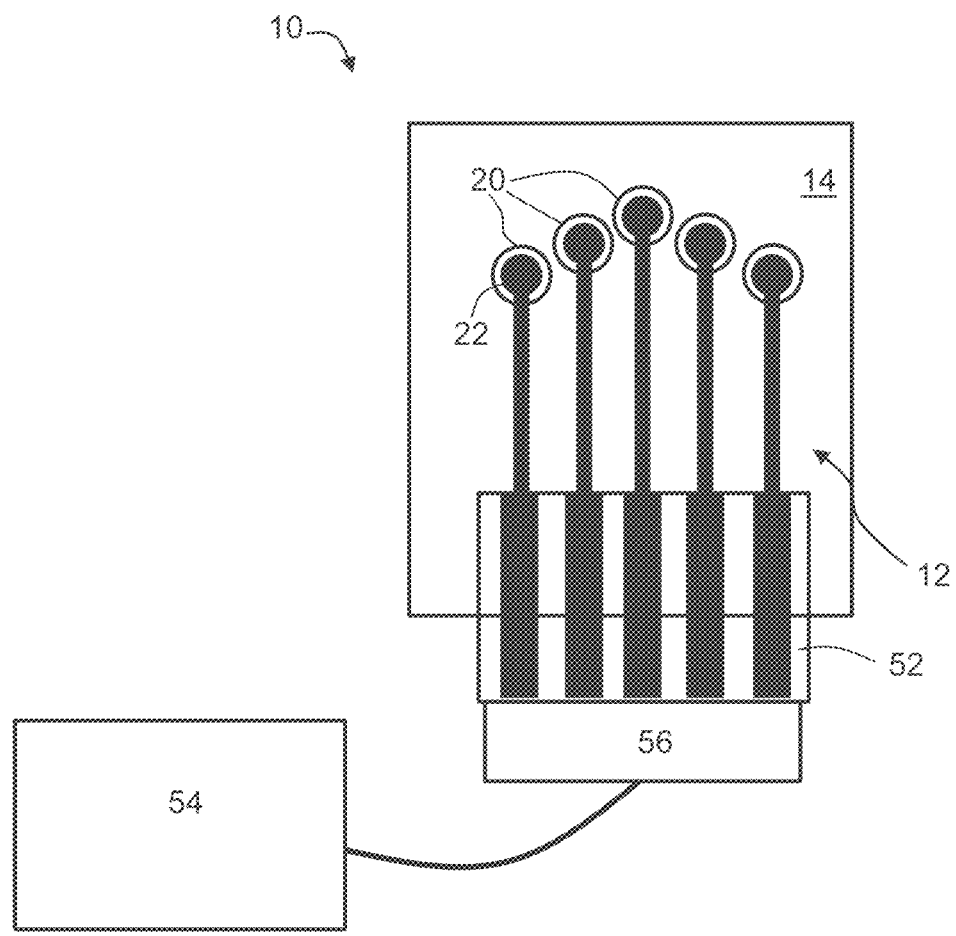
FIG. 1 is a schematic illustration of a sensing device, according to some embodiments of the present invention.

The present invention, in some embodiments thereof, relates to sensing of physiological data and, more particularly, but not exclusively, to a sensing electrode and method of fabricating the same.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In a search for sensing electrode and method of fabricating sensing electrode, particularly but not exclusively, for EEG, EMG, ECG and/or EOG, the present Inventors realized that long-term, multi-site recording is difficult, for example, because of poor signal transmission at the electrode-skin interfaces and its instability over long time periods. In conventional application of surface electrodes, skin preparation (wiping the skin with alcohol and skin abrasion) as well as improved electrode positioning and the application of an electrolytic gel are desired. The present Inventors realized that the application of electrode to the skin is time consuming, demands the presence of a specialized technician, uncomfortable and may even be painful. The present Inventors further realized that gels and adhesive pastes are typically non-sterile and may cause skin irritation, and that short circuits between adjacent electrodes due to gel leakage can also occur. The present Inventors additionally realized that the signal quality gradually degrades over time as the skin regenerates and/or the conductive gel dries.

The present Inventors have therefore devised a sensing electrode that can optionally and preferably operate without use of artificial wet, such as, but not limited to, impedance matching medium or gel, between the electrodes and the skin. Optionally and preferably, the sensing electrode is manufactured by printing, e.g., by screen-printing or inkjet printing.

Screen-printing allows electrode patterning into a desired electrode shape, a wide range of possible inks (e.g., gold, silver, silver chloride, carbon and the like), at relative high resolution, and flexibility in choosing the substrate material (e.g., plastic sheets, cloth and the like). In some embodiments of the present invention an array of the electrodes is mounted on or integrated with a headset, such as, but not limited to, a headset used during a medical procedure, e.g., a Deep Brain Stimulation procedure, or any other procedure applied to the head.

FIG. 1 is a schematic illustration of a sensing device 10, according to some embodiments of the present invention. Sensing device 10 comprises an array 12 of electrodes, optionally and preferably dry electrodes. In some embodiments of the present invention on or more of the electrodes of array 12, e.g., all the electrodes of array 12, are coated. For example, one or more of the electrodes, e.g., all the electrodes, can be a metallic electrode which is coated or partially coated by a polymer.

The metallic electrode can be made of any metal, including, without limitation, gold, silver, platinum, copper, rhodium, iridium, tungsten, molybdenum, palladium, ruthenium and osmium. More preferred metals include, without limitation, carbon, silver, and silver chloride.

The polymer optionally and preferably comprises a plasma polymerized monomer. Representative examples of such monomers include, without limitation, a thiophene, a pyrrole, an aniline, and substituted derivatives thereof.

Useful thiophenes include unsubstituted and substituted thiophene, such as those described in U.S. Pat. Nos. 4,959,430 and 4,910,645 the contents of which are hereby incorporated by reference. A preferred substituted thiophene includes 3,4-ethylenedioxythiophene.

Useful pyrroles, include, without limitation, unsubstituted pyrrole and the substituted pyrroles such as N-alkylpyrroles, N-arylpyrroles, the monoalkyl to the carbon atoms or dialkyl substituted pyrroles, and the monohalogen to the carbon atoms or dihalo-substituted pyrroles. A pyrrole can be used alone or in combination with others, so that copolymers are formed in incorporated various pyrroles. The recurring units are optionally and preferably derived pyrrole in the copolymers essentially of from unsubstituted pyrrole itself. Substituted pyrroles be used in the production, for this purpose, the 3,4-dialkyl are pyrroles, in particular those having 1 to 4 carbon atoms in the alkyl radical, such as 3,4-dimethylpyrrole and 3,4-diethylpyrrole, as well as the 3,4-dihalo pyrroles, and 3,4-dichloropyrrole.

Useful anilines include, without limitation, p-anisidine, 4'-aminoacetanilide, p-hydroxy-N,N-dimethylaniline and o-phenylenediamine, p-p'biphenol, 4'-hydroxyacetanilide, p-methoxyphenol, p-anisidine and 4'-aminoacetanilide.

In some embodiments of the present invention the electrodes form a pattern of nanostructures.

The term "nanostructure," as used herein, refers to a structure having a highest dimension which is above 1 nm and less than 100 nm or less than 50 nm, or less than 40 nm, e.g., from about 3 nm to about 30 nm or from about 5 nm to about 15 nm.

As used herein the term "about" refers to ±10%.

Typically, the nanostructure is elongated.

The term "elongated nanostructure" generally refers to a three-dimensional body made of a solid substance, in which one of its dimensions is at least 2 times, or at least 10 times, or at least 50 times e.g., at least 100 times larger than any of the other two dimensions. The largest dimension of the elongated solid structure is referred to herein as the longitudinal dimension or the length of the nanostructure, and the other two dimensions are referred to herein as the transverse dimensions. The largest of the transverse dimensions is referred to herein as the diameter or width of the elongated nanostructure. The ratio between the length and the width of the nanostructure is known as the aspect ratio of the nanostructure.

In some embodiments of the present invention the elongated nanostructure has, at any point along its length, at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the elongated nanostructure has at least one cross-sectional dimension ranging from 0.5 nanometers to 200 nanometers, or from 1 nm to 100 nm, or from 1 nm to 50 nm.

The length of an elongated nanostructure expresses its elongation extent generally perpendicularly to its cross-section. According to some embodiments of the present invention, the length of the nanostructure ranges from 10 nm to 50 microns. In various exemplary embodiments of the invention the length of the elongated nanostructure is at least 100 nm, or at least 500 nm, or at least 1 µm, or at least 2 µm, or at least 3 µm, e.g., about 4 µm, or more.

The cross-section of the elongated semiconductor may have any arbitrary shape, including, but not limited to, circular, square, rectangular, triangular and elliptical. Regular and irregular shapes are included.

The width of the elongated nanostructure is preferably less than 1 µm. In various exemplary embodiments of the invention the width of the nanostructure is from about 5 nm to about 200 nm, more preferably from about 5 nm to about 100 nm.

The present embodiments contemplate many any type of nanostructure.

For example, in some embodiments of the present invention the nanostructures are carbon nanotubes (CNTs). The present embodiments contemplate any type of carbon nanotube, including without limitation, a single-walled nanotube (SWNT) which can be considered as a long wrapped graphene sheet and a multi walled nanotube (MWNT) which can be considered as a collection of concentric SWNTs with different diameters.

In some embodiments of the present invention, the nanostructures are organic nanostructures.

The term "organic nanostructure" refers to a nanostructure made at least in part of organic substance. As used herein, the phrase "organic substance" describes any substance that comprises carbon and hydrogen atoms, with or without additional elements.

In some embodiments of the present invention sensing device 10 comprises a double sided adhesive film 14. In these embodiments, the electrodes of array 12 are attached to one side of film 14, and the opposite side of film 14 is attachable to a surface (not shown) at which sensing signals are to be measured. Optionally film 14 comprises a plurality of opening 20 to expose a sensing portion 22 of each electrode of array 12. Device 10 optionally and preferably comprises an electrical coupler 52 for connecting the electrodes of array 12 to a measuring device 54. The electrical coupler 52 is preferably compatible with a matched socket 56, e.g., a Low-Insertion Force (LIF) socket or, more preferably a Zero-Insertion Force (ZIF) socket. An additional protective layer (not shown) can optionally and preferably be applied on the passivation film to protect the electronic parts from liquids.

Preferably, the sensing electrode of the present embodiments exhibits low skin-electrode impedance at low geometric areas. The reduction in impedance is advantageous because it allows efficient and high resolution recording and stimulation. The sensing electrode of the present embodiments can be placed on the skin for long duration (e.g., several hours or days) in a stable manner.

An electrode array can be formed, for example, by forming a pattern, e.g., a pattern of nanostructures or other conductive pattern, on a work substrate, and then transferring the pattern, e.g., by contact, onto a solid support, optionally and preferably a flexible solid support, that is attachable to the skin. The solid support can be for example, a medical adhesive tape, polydimethylsiloxane (PDMS), Parylene C, polyimide or the like. The advantage of using a pattern on one printed layer for the electrodes of the present embodiments is that such a pattern can form a seamless circuit in which the risk of delamination and formation of cracks is reduced or eliminated. These embodiments are particularly useful for long term use.

Preferably, the electrode-skin impedance is improved by a plasma polymerization process which enhanced the capacitive properties of the electrodes. Plasma polymerization is preferred because it is a simple, solvent free, room temperature process that can be used to obtain ultrathin films onto a variety of substrates. Plasma Polymerization involves a glow discharge, generated by applying an electric field on a monomer gas at low pressure. The interaction of the monomer fragments with the substrate results with polymer deposition. The chemical structure of the final polymer film, the morphology and the physical properties depends on polymerization conditions (power, monomer vapor pressure and deposition time). While these films lack ordered chains, they have many benefits including the deposition of ultrathin, pinhole-free, uniform films with high adhesion to a variety of substrates such as polymers, glass and metal surfaces.

Preferably, the electrodes are coated by plasma polymerization under low pressure, for example, below 1 mbar, or below 0.5 mbar, or below 0.25 mbar, or below 0.125 mbar, e.g., 0.1 mbar or less. In some embodiments, the plasma polymerization is at frequency in a radiofrequency (RF) range. In experiments performed by the present Inventors a frequency of 13.56 MHz was employed.

As demonstrated in the Example section that follows, plasma polymerized film improves the electrode electrochemical capacitance (measured in phosphate-buffered saline) by 1-2 orders of magnitude, comparable with that of non-Faradaic porous electrodes with specific capacitance $C_s$ in the range of 2 $mFcm^{-2}$ for TiN and 3-10 $mFcm^{-2}$ for carbon nanotube. Further demonstrated is sensitivity of the sensing electrode to force and facial expression by multi-site sEMG recording from the palm and face muscles.

The sensing electrode of the present embodiments is preferably a soft and dry and is skin-adhesive. The sensing electrode of the present embodiments can be used in numerous applications such as, but not limited to, brain-machine interfacing, muscle diagnostics (e.g., long-term muscle diagnostics), post-injury rehabilitation, gaming, neurological and psychological assessment, bio-feedback, neuro-feedback, and the like. It was found by the present Inventors that high Signal-to-Noise Ratio (SNR) can be achieved without the need for electrolytic gel, even for nonmetallic electrodes. This is counterintuitive, since conventional metallic electrodes mandate use of gel for improving the SNR. Without wishing to be bound to any particular theory, it is believed that the high signal to noise of the electrodes of the present embodiments is due to the conformity of the electrode with the skin's shape.

Figure 2:
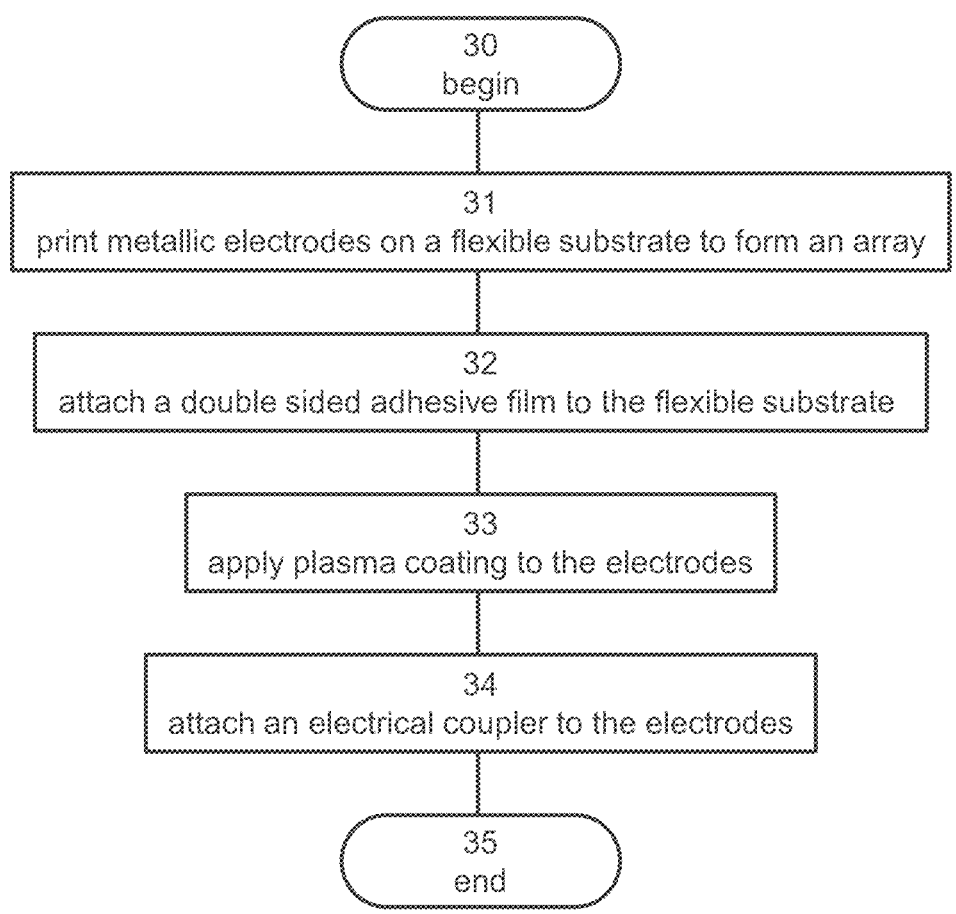
FIG. 2 is a flowchart diagram of a method suitable for fabricating a sensing device according to various exemplary embodiments of the present invention.

FIG. 2 is a flowchart diagram and FIGS. 3A-F are schematic process illustrations of a method suitable for fabricating a sensing device according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Figure 3A:
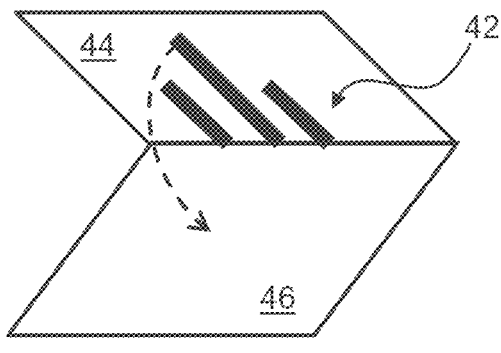
FIGS. 3A-F are schematic process illustrations of the method of FIG. 2.
Figure 3B:
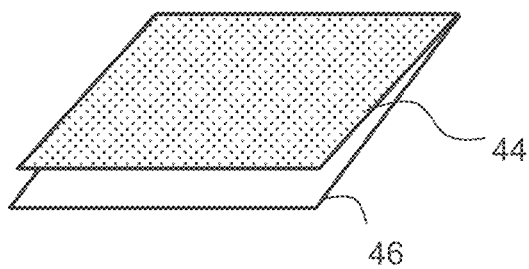
Figure 3C:
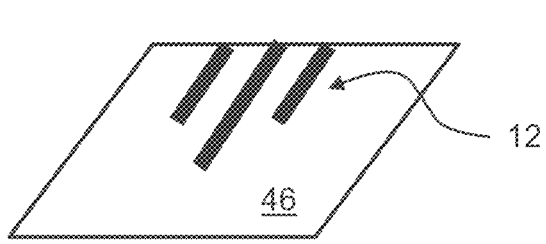

The method begins at 30 and optionally and preferably continues to 31 at which metallic electrodes are printed on a flexible substrate to form array 12. This can be done, for example, by screen printing as illustrated in FIGS. 3A-C, where FIG. 3A shows a conductive pattern 42 formed on a work substrate 44 before the pattern 42 is transferred to a flexible substrate 46, FIG. 3B shows a process in which contact is established between work substrate 44 and flexible substrate 46, to transfer pattern 42 to flexible substrate 46, and FIG. 3C shows the array 12 that is the result of the transfer. In some embodiments of the present invention flexible substrate 46 is cut, for example, by laser cutting to accommodate skin curvature and to prevent or reduce wrinkles once the device is applied to the skin.

Figure 3D:
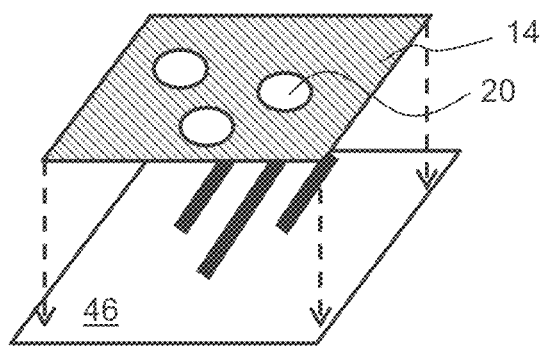
Figure 3E:
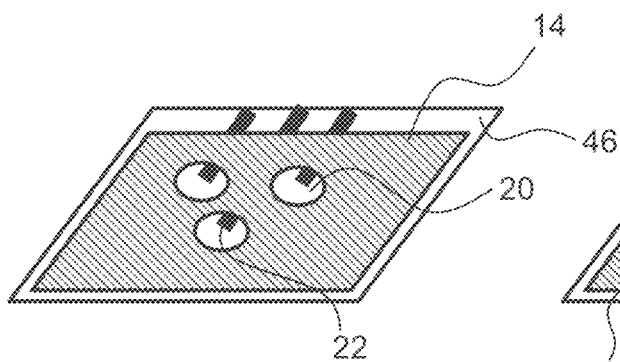

The method optionally and preferably continues to 32 at which a double sided adhesive film is attached to the flexible substrate 46. This is illustrated in FIGS. 3D and 3E, where FIG. 3D shows an adhesive film 14 with a plurality of openings 20, and FIG. 3E shows adhesive film 14 once attached to substrate 46, such that the sensing portions 22 of the electrodes of array 12 are expose at the openings. Preferably, adhesive film 14 is attached to flexible substrate 46 such that the bases of the electrodes remain exposed, as illustrated in FIG. 3D.

The method optionally and preferably continues to 33 at which plasma coating is applied to the metallic electrodes, to induce polymerization of a monomer to a polymer onto the electrodes. The plasma coating is optionally and preferably characterized by low monomer vapor pressure, e.g., below 1 mbar, or below 0.5 mbar, or below 0.25 mbar, or below 0.125 mbar, e.g., 0.1 mbar or less. In some embodiments, the plasma polymerization is at frequency in a radiofrequency (RF) range. In experiments performed by the present Inventors a frequency of 13.56 MHz was employed. In some embodiments of the present invention the plasma polymerization is characterized by plasma power of from about 10 W to about 100 W.

Figure 3F:
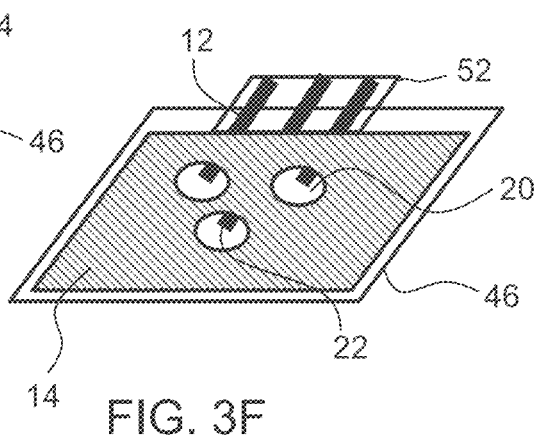

The method can optionally continue to 34 at which an electrical coupler is attached to the base of electrodes. This is illustrated in FIG. 3F, showing electrical coupler 52 connected to array 12. The electrical coupler 52 is preferably compatible with a matched socket (not shown, see FIG. 1).

The method ends at 35.

The present embodiments are useful in many applications. For example, the device of the present embodiments can be used for recording signals from the palm (e.g., the first dorsal interosseous). This is advantageous, for example, in brain-machine interfacing. As the force applied by the index finger can be readily derived from the sEMG amplitude, sEMG data can be conveniently transformed into a simple communication platform, without the need for a mechanical device.

The device of the present embodiments can be used for recording facial expressions. This is advantageous, for example, for recording emotions, and for digitizing emotions for clinical and social purposes. It may be used also for facial muscle rehabilitation and diagnostics, for monitoring proper muscle activation, and for assessing neurological or psychological disorders.

The device of the present embodiments can also be used for sleep analysis. For example, the device can be used for recording signals such as, but not limited to, EEG, EOG and/or EMG signals, and the signals can then be analyzed for determining one or more sleep stages (e.g., REM sleep) as disclosed, for example, in U.S. Pat. No. 7,623,912 the contents of which are hereby incorporated by reference.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

The present Example describe soft carbon screen-printed electrodes (SPEs), which can be placed on the skin for a long duration (from several hours to a few days) in a stable manner, with low electrode-skin impedance, even at low geometric areas. The impedance reduction is advantageous for high signal to noise ratio (SNR), and high-resolution recordings. The electrode-skin impedance was improved by a plasma polymerized 3,4-ethylenedioxythiophene (ppE-DOT) coating. Plasma polymerization was chosen as a simple, solvent-free, room temperature process. EDOT was selected owing to its biocompatibility and ionic conductivity. The present Example demonstrates that the plasma polymerized film improves the electrode capacitance, yielding a capacitance comparable with conventional neuronal electrodes. The present Example shows multi-site sEMG recordings from the hand and face and demonstrates force and facial expression sensitivity.

Methods

Fabrication of Screen-Printed Electrode Array

Electrodes were realized following the scheme presented in FIGS. 4A-F. The process builds on screen-printing, combined with laser cutting to make holes in a double-sided passivation layer, which also serves as a skin-adhesive material. FIGS. 4A and 4B illustrate screen-printing onto a temporary tattoo sheet, FIG. 4C illustrates electrode array after printing. A double-sided adhesive film was cut with a laser to form a passivation layer (FIG. 4D). FIG. 4E illustrates the passivation and the electrode array once aligned and bonded. A plasma coating process was then applied, and a polyimide film with holes was glued to the array to fit into a zero insertion force (ZIF) socket (FIG. 4F).

The electrodes were fabricated using a pre-patterned mesh stencil (Sefar Inc.). Printing was accomplished by a manual application of a conductive carbon ink (Conductive compounds) on a blank temporary tattoo paper (Papilio), which served as a substrate. This was followed by curing at about 130° C. for about 10 min. The electrical resistance of the carbon film was about 40Ω/□. A double-sided adhesive layer (Papilio) was used as a passivation layer. A laser cutter (ELAS Ltd.) was used to define holes for the exposed electrode area. A two-step process was used to prevent overheating of the glue layer: (1) laser intensity of about 400 mW and removal of the passivation upper layer, followed by (2) intensity of about 800 mW and removal of the remaining two layers. The adhesive passivation layer with pre-defined holes and the printed electrode were pressed together. To mechanically support contact of the printed electrode array and a ZIF connector (Omnetics), a polyimide tape (Kapton, 3 M) with pre-defined holes was added onto the array bonding pads. The holes in the Kapton film were cut with the same laser cutter with intensity of about 400 mW.

EDOT (Sigma) was plasma polymerized using an RF plasma system (Pico-RF-PC, Diener electronics), operating at a frequency of about 13.56 MHz and a monomer vapor pressure of about 0.1 mbar. Plasma power of either about 12 W or about 90 W for either about 10 or about 60 min was used.

Electrochemical Characterization

Cyclic voltammetry (CV) and (electrochemical impedance spectroscopy) EIS were performed in PBS (Sigma).

CV measurements were conducted using a potentiostat (263A, Princeton Applied Research) under ambient conditions, using a three-electrode cell configuration with an Ag/AgCl reference electrode. DC capacitance was calculated from the slope of the current versus the scan rate according to: $i = CdV/dt$, where i is the current, C is the DC capacitance and dV/dt is the voltage scan rate.

EIS measurements were conducted under equilibrium conditions by applying 10 mV AC signals using a lock-in amplifier (SR830, Stanford Research Systems) and a potentiostat (263A, Princeton Applied Research). SPE test samples (Dropsens) were used for electrochemical characterization in phosphate-buffered saline (PBS).

Electrode-skin impedance was measured using an amplifier evaluation system (RHD2000, Intan). Pregelled electrodes (Spes Medica) were used for testing (15 by 20 mm) and as reference (35 by 45 mm).

Surface Properties

X-ray photoelectron spectroscopy (XPS) measurements were performed using a 5600 Multi-Technique System (Physical Electronics). Structural characterization of the printed electrode surface was performed using scanning electron microscope (SEM) (JEOL JSM-6700 F).

Electrophysiology sEMG recordings were performed using an Intan Technologies amplifier evaluation board (RHD2000). The skin was cleaned (everi, Spesmedica) and dried prior to electrode placement. Force calibration measurements were performed by applying a force against a calibrated spring using the index finger. Noise RMS levels were calculated during the muscle's relaxation time. SNR was calculated by dividing signal RMS levels (calculated over the period of activation) by noise RMS (2 s window).

Experiments on Human Subjects

All experiments on human skin were conducted on volunteers in accordance with relevant guidelines and regulations under approval from the Institutional Ethics Committee Review Board at Tel Aviv University, Israel. Informed consent was obtained from all subjects.

Results

FIGS. 5A-C are images showing the fabricated array once placed on a hand of a human volunteer. Red arrows highlight the polyimide film (FIG. 5A), ZIF socket with custom-made printed circuit board (PCB) (FIG. 5B), and a hole in the passivation layer (FIG. 5C). The conformal contact allowed stable recordings even for small electrodes (20 mm$^2$).

Figure 6A:
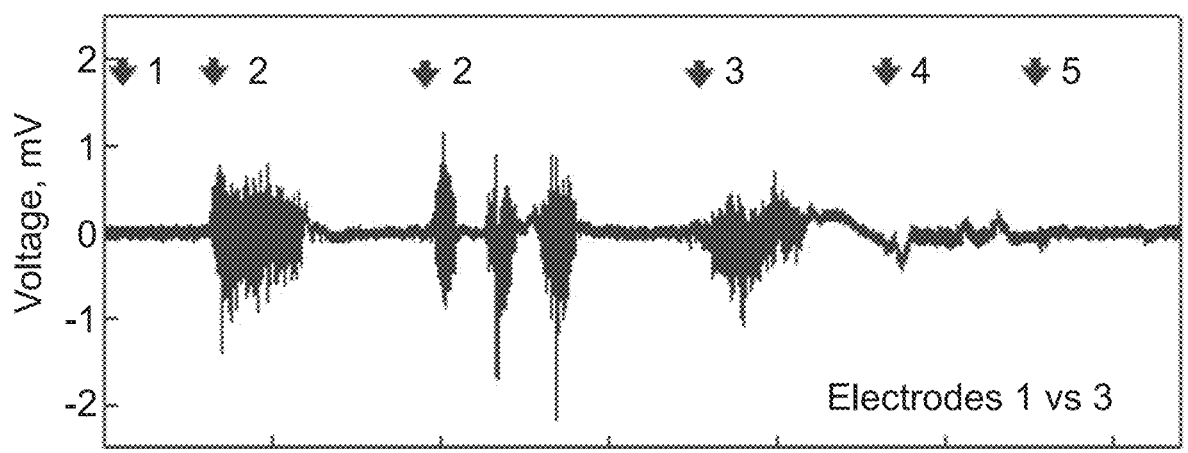
FIGS. 6A-C show sEMG recording of the first dorsal interosseous (FDI), as obtained in experiments performed according to some embodiments of the present invention.
Figure 6B:
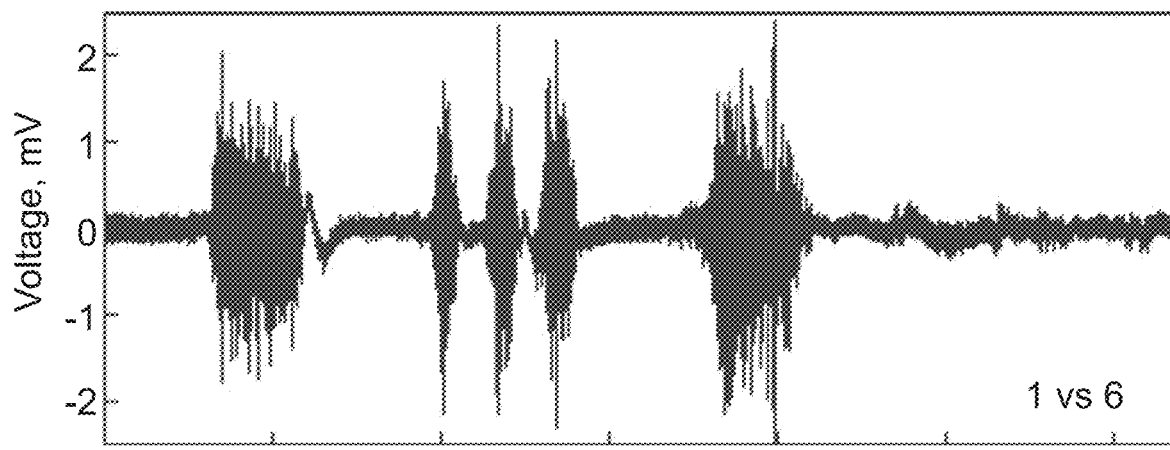
Figure 6C:
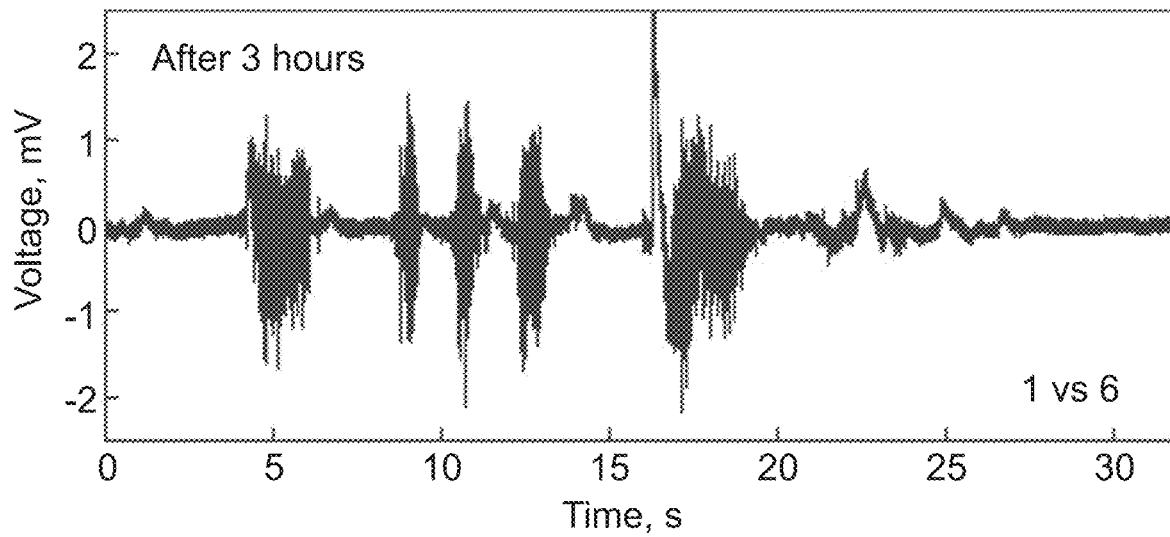

FIGS. 6A and 6B show sEMG recording of the first dorsal interosseous (FDI) using ppEDOT/carbon electrodes, where FIG. 6A shows sEMG recording for electrode No. 1 versus electrode No. 3, and FIG. 6B shows sEMG recording for electrode No. 1 versus electrode No. 6, and. The arrows indicate: (1) rest position followed by (2) force application (isometric contractions) on the FDI for 2.5 s and 1 s (repeated three times). (3) Flexion of the index finger towards the thumb, (4) from the thumb and (5) pointing up. The electrodes stability was verified by leaving it on the hand for an extended duration and repeating the recording under the same protocol. FIG. 6C show the sEMG recording obtained for electrode No. 1 versus electrode No. 6 after 3 hours. As shown, recordings remained stable after 3 hours, with a SNR value of 13 (22 dB).

Figure 7A:
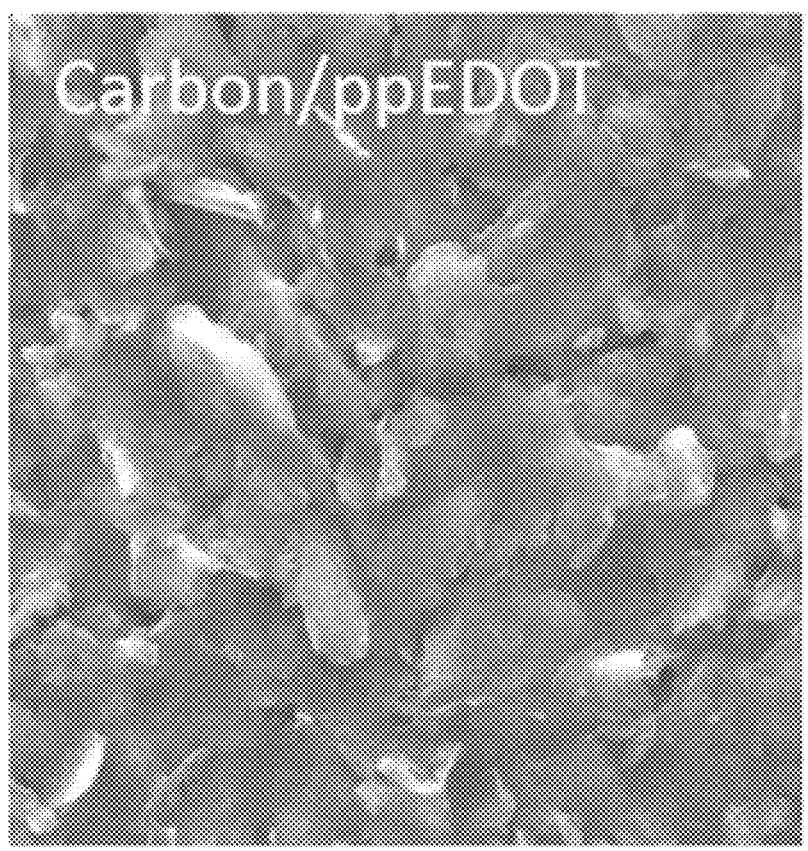
FIGS. 7A and 7B are SEM images of electrode surfaces as obtained in experiments performed according to some embodiments of the present invention.
Figure 7B:
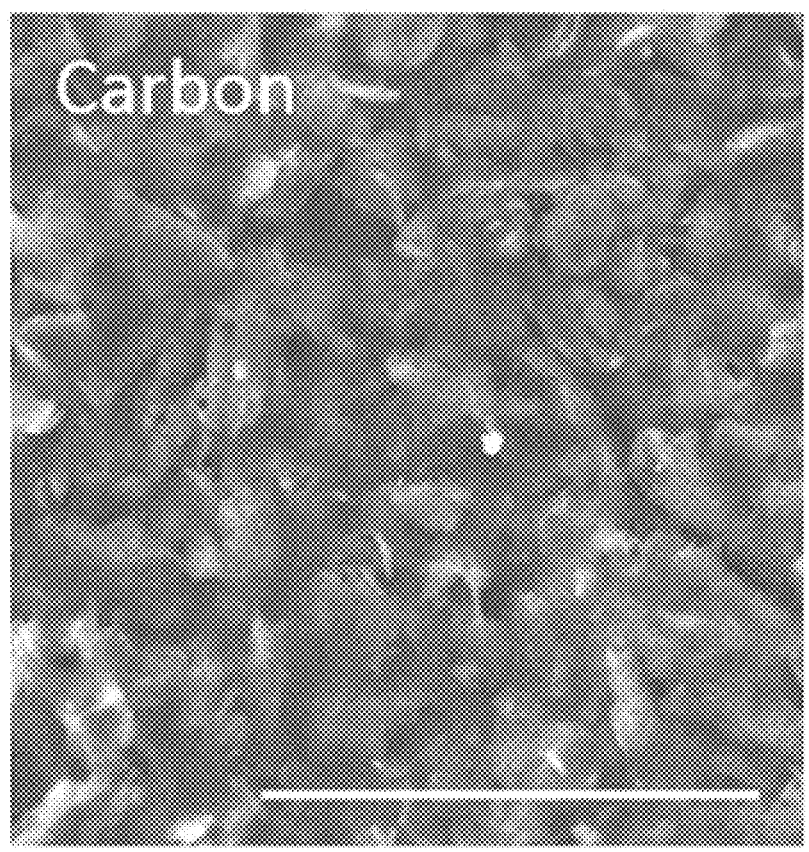

FIG. 7A is a SEM images of a ppEDOT coated carbon electrode surface, and FIG. 7B is a SEM images of an uncoated electrode. Scale bar is 50 µm. The morphology the two types of surfaces appeared similar, indicating an ultra-thin coating.

The plasma polymerization process was characterized, focusing on chemical and impedance spectroscopy analysis.

Figure 8A:
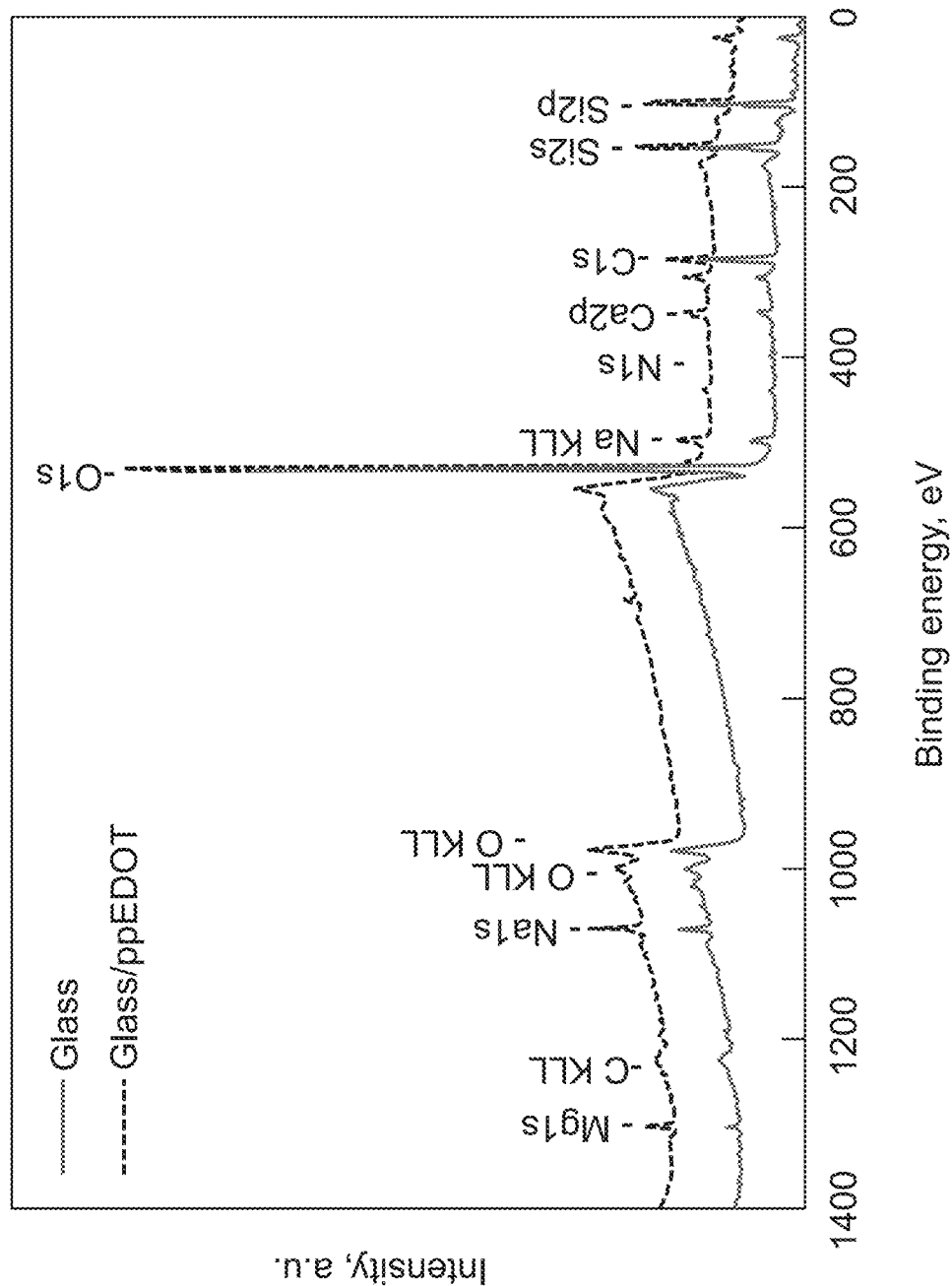
FIGS. 8A-C show XPS spectra on glass compared with an uncoated glass (FIG. 8A), detailed spectra at different plasma deposition power and duration (FIG. 8B), and XPS spectra on a carbon electrode compared with an uncoated electrode surface (FIG. 8C), as obtained in experiments performed according to some embodiments of the present invention.
Figure 8B:
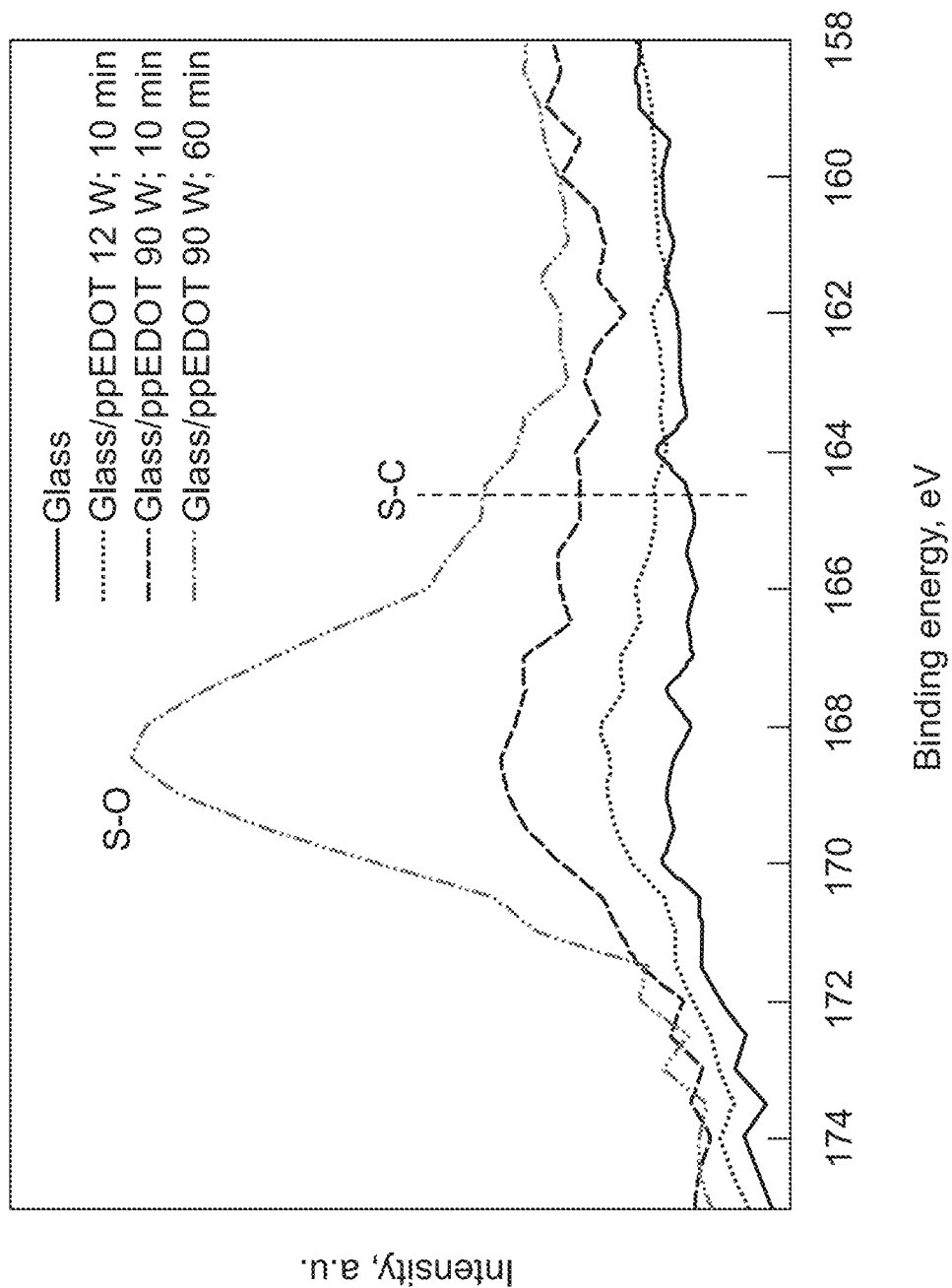
Figure 8C:
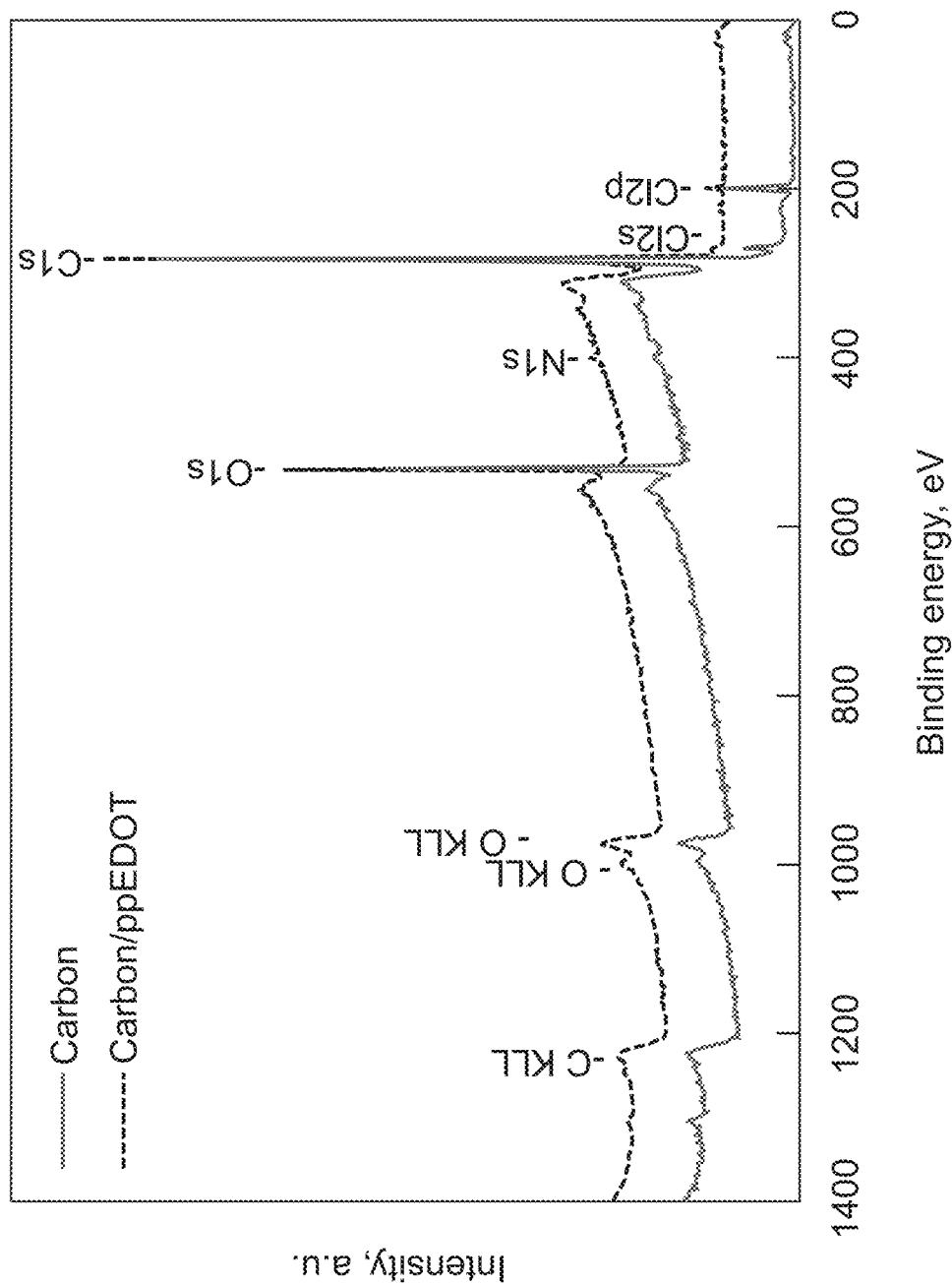

The chemical structure, morphology and physical properties of the film depends on process conditions (power, monomer vapor pressure and deposition time). The process employed in the present Example achieved substantial impedance reduction. FIG. 8A shows XPS spectra (90 W; 10 min) on glass compared with an uncoated glass, FIG. 8B shows detailed spectra at different plasma deposition power and duration, and FIG. 8C shows XPS spectra (90 W; 10 min) on a carbon electrode compared with an uncoated electrode surface. An increase in sulfur and oxygen components from 0.05% to 0.32% and from 53.3% to 56.6% respectively indicates ppEDOT deposition (FIG. 8B). The atomic ratio of sulfur, as well as the concentration of C—S and S—O components, increased with process time and power. ppEDOT coated carbon SPEs (FIG. 8C) revealed an increase in surface oxygen from 15.2% to 18.6%, indicating the formation of a film incorporating elements from the monomer, while not retaining the monomer chemical structure, was likely due to fragmentation in the plasma environment.

For validating the biocompatibility of the coating, comparative in vitro cell survival tests were conducted. Primary neurons were cultured on glass coated with ppEDOT, and their survival was compared with that of cells seeded on a poly-D-lysine coating (a cell adhesion promoting protein), and on uncoated surfaces. No significant differences were found in cell survival up to six days. The electrochemical properties of pristine and ppEDOT SPEs were explored using CV and EIS in PBS.

Figure 9A:
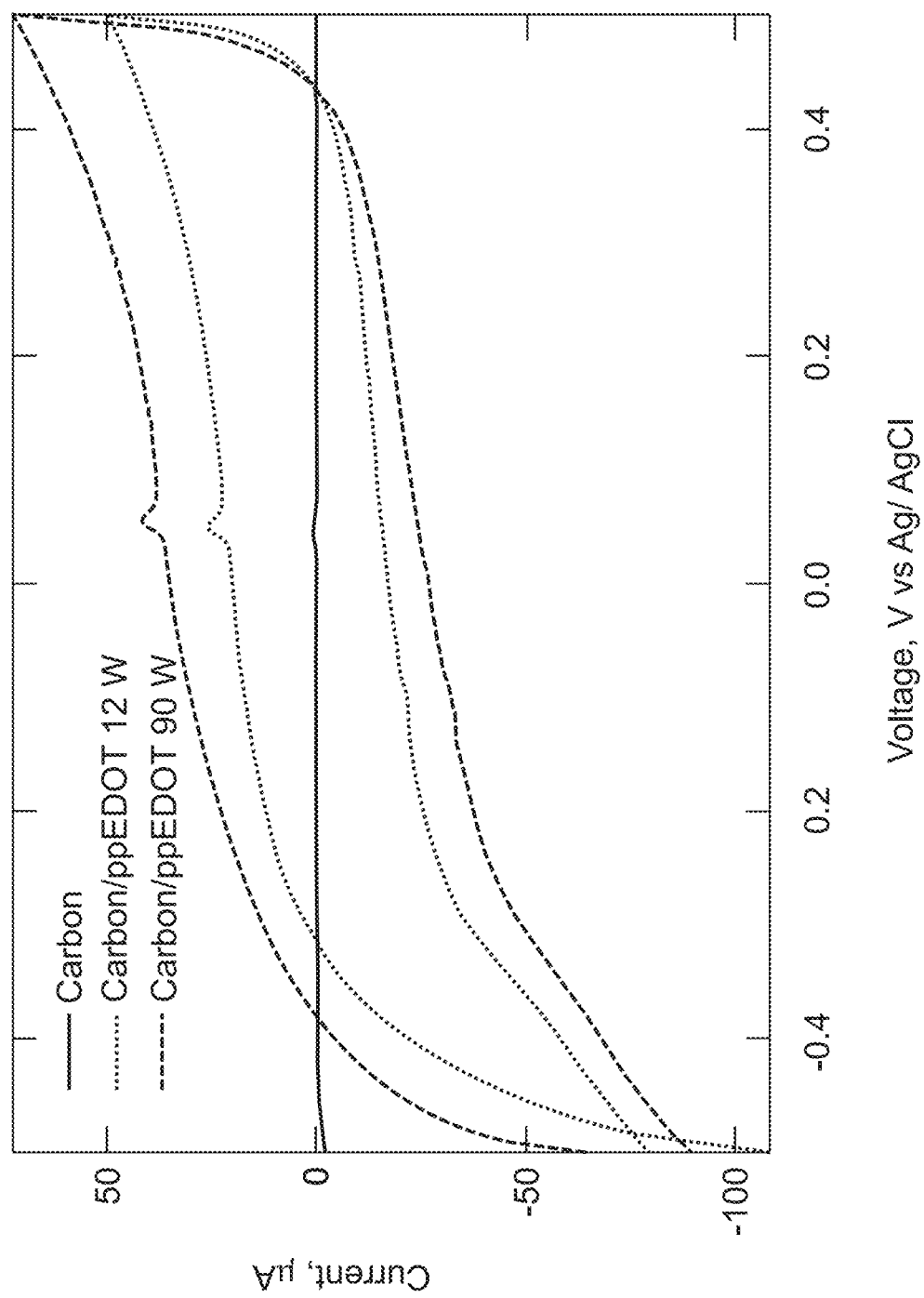
FIGS. 9A and 9B show CV scans in PBS of ppEDOT electrodes under different deposition power (FIG. 9A), and EIS scans at different deposition powers (FIG. 9B), as obtained in experiments performed according to some embodiments of the present invention.
Figure 9B:
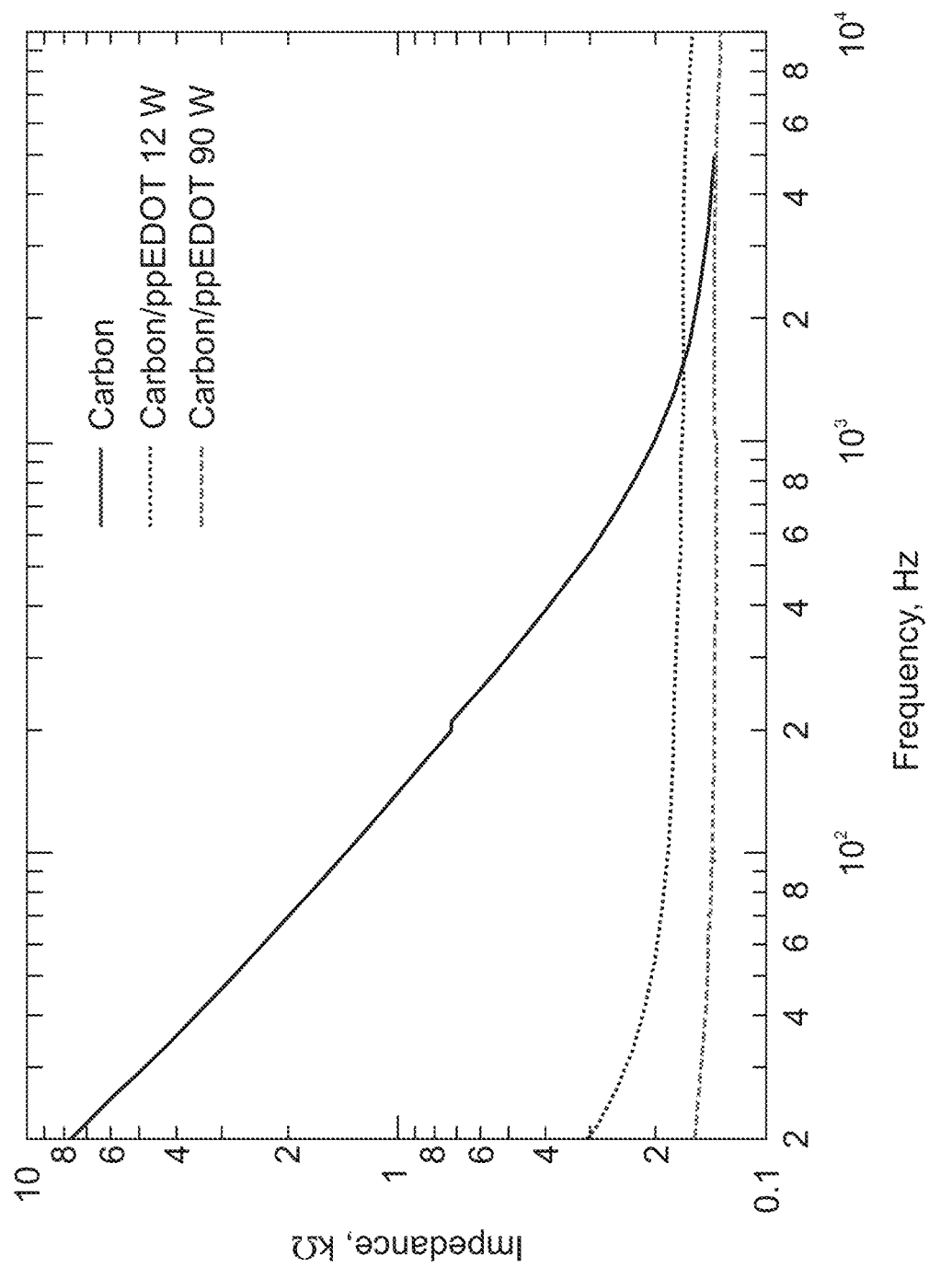

FIGS. 9A and 9B show CV scans in PBS (50 mVs$^{-1}$) of ppEDOT electrodes under different deposition power (pristine, 12 and 90 W; 10 min) (FIG. 9A), and EIS scans in PBS at different deposition powers (pristine, 12 and 90 W; 10 min), (FIG. 9B).

Figure 10A:
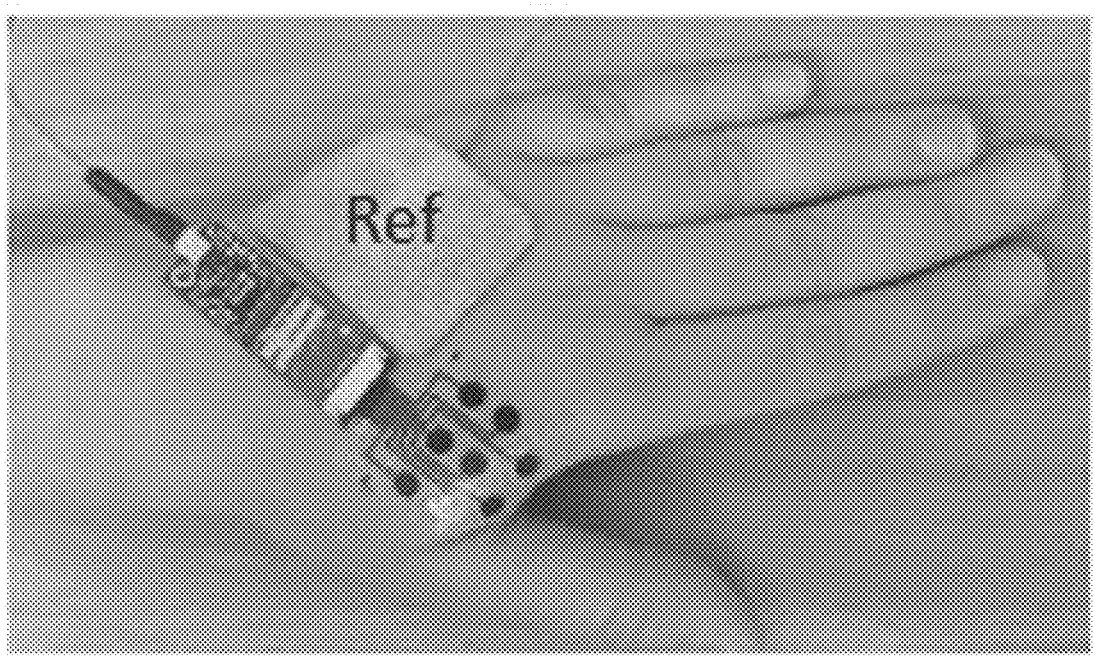
FIGS. 10A-B show images of electrodes of the present embodiments (FIG. 10A), and commercially available electrodes (FIG. 10B), placed on the hand above the FDI, as obtained in experiments performed according to some embodiments of the present invention.
Figure 10B:

FIGS. 10A-B include an image of the SPE of the present embodiments (FIG. 10A), and an image of commercially available electrodes (FIG. 10B), placed on the hand above the FDI, with a ground electrode placed above the fourth and fifth metacarpals.

Figure 11:
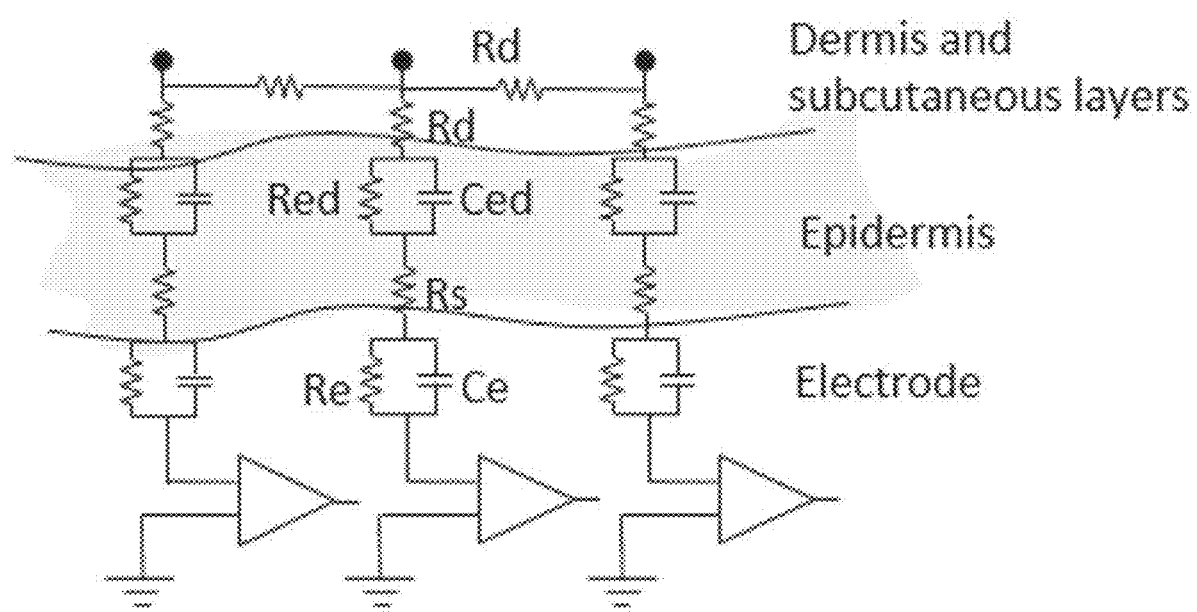
FIG. 11 is a schematic illustration of an electrode-skin equivalent circuit model.

FIG. 11 is an electrode-skin equivalent circuit model, where $R_e$ and $C_e$ represent the resistive and capacitive components of the electrode, $R_{ed}$, $C_{ed}$ and $R_d$ represent the RC elements of the epidermis and dermis layers, $R_s$ represents an effective serial resistance at the interface (e.g., gel or sweat).

Figure 12:
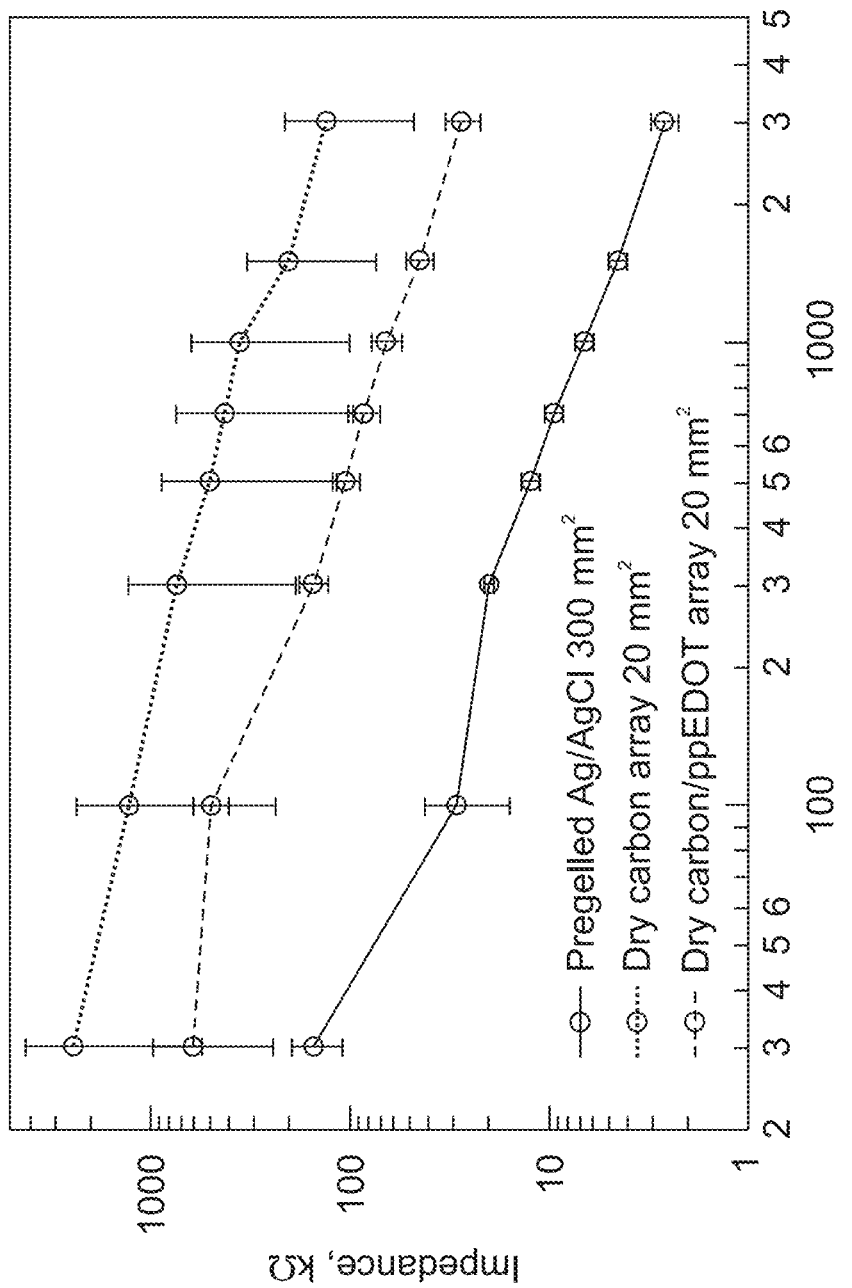
FIG. 12 shows average electrode-skin impedance as a function of the frequency, as obtained in experiments performed according to some embodiments of the present invention.

FIG. 12 shows average electrode-skin impedance as a function of the frequency for the commercially available electrode (n=8), the carbon electrode (n=20), and the carbon/ppEDOT (90 W for 10 min; n=13) electrode, where n denotes the number of tested electrodes.

The CV data (FIG. 9A) revealed featureless curves for uncoated and coated electrodes (the small oxidation peak at 0.1 V is typical to carbon ink due to impurities). Current versus scan rate showed linear dependence in accordance with a double layer capacitor model. The DC capacitance was calculated and normalized with the electrode area (about 12 mm$^2$) to derive the specific capacitance ($C_s$). $C_s$ increased by two orders of magnitude from 0.018 to 1.6±0.1 and 3.3±0.2 mFcm$^{-2}$ for coated electrode (12 W and 90 W, respectively). 1-3 mFcm-2 values are comparable with conventional porous titanium nitride and carbon nanotube electrodes (with 2-10 mFcm$^{-2}$). The electrode impedance appears to stabilize, especially the carbon/ppEDOT, at moderate frequencies to a typical value reflecting the PBS impedance (FIG. 9B).

The electrode-skin impedance of SPE and commercially available electrodes were studied under similar conditions. The skin was abraded (and wiped) prior to positioning of all electrode types using a designated abrasive paste. The skin preparation procedure was identical for both pregelled and dry electrodes. At 1 kHz, coated electrodes have on average 10 times lower impedance than that of pristine electrodes, which in turn have about 10 times larger impedance than that of gelled electrodes. Since the commercially available electrodes have 15 times the area, it appears that their specific impedance is similar to that of dry ppEDOT/carbon electrodes of the present embodiments.

Figures 14A, 14B, 14C:
FIGS. 14A-G show graphs obtained during the functional recordings.
Figure 14D:
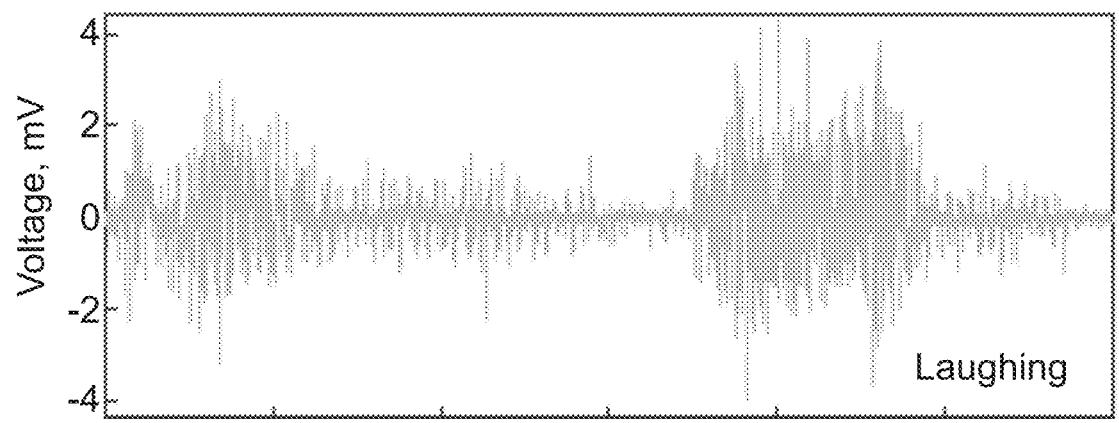
Figure 14E:
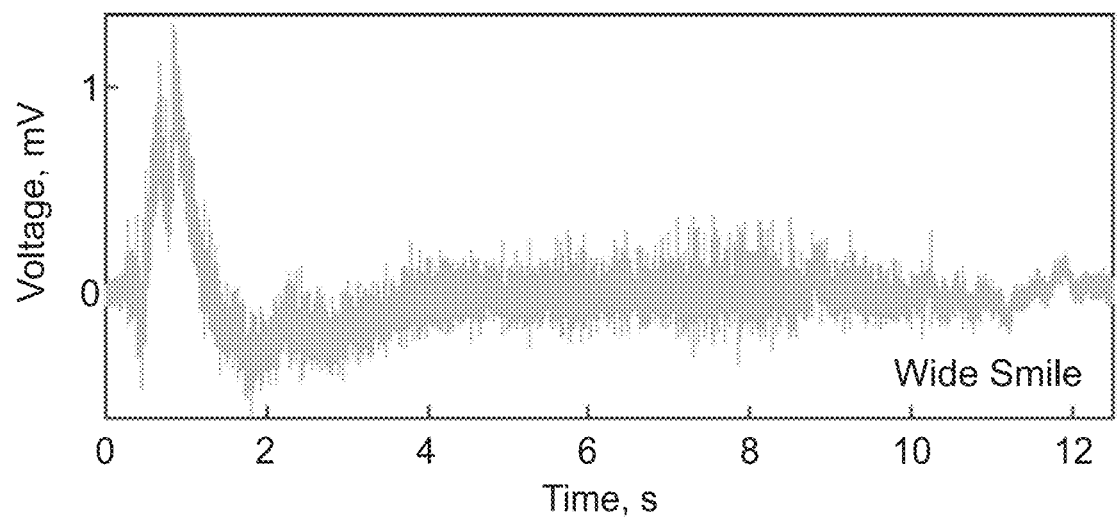
Figures 14F, 14G:
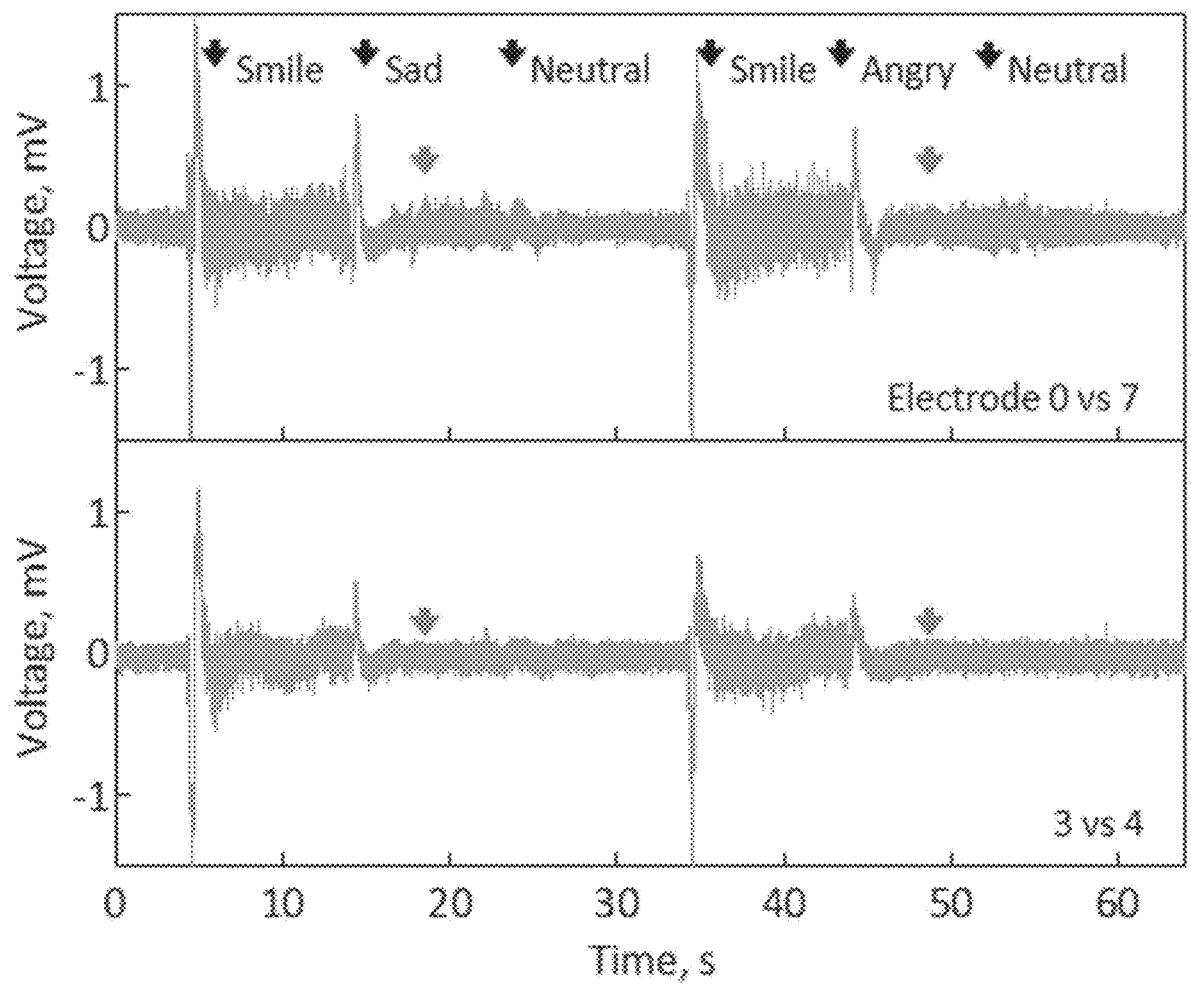

The linear correlation between the impedance and the inverse of electrode surface area was validated by testing electrodes at different sizes. To demonstrate the performances of the electrodes, two scenarios were considered: long-term recording from the FDI, and from the zygomaticus major (ZM) muscle of the face. FIGS. 13A-B and 14A-G show images (FIGS. 13A and 14A-C) and graphs (FIGS. 13B and 14D-G) obtained during the functional recordings. FIG. 13A shows sEMG skin electrodes application for recording FDI activity, FIG. 13B shows FDI activity at different forces measured with a calibrated spring, FIGS. 14A-C show electrode array placed above the ZM of the face during natural (FIG. 14A), smile (FIG. 14B) and sad (FIG. 14C) expressions, FIGS. 14D and 14E show recorded signals distinguishing between a wide smile (FIG. 14E) and a laughing (FIG. 14D) expression, and FIGS. 14F and 14G show differentiation during neutral, smiling, sad and angry facial expressions, using electrode Nos. 0 vs 7 (FIG. 14F) and using electrodes Nos. 3 vs. 4 (FIG. 14G).

Immediately after placing the array, stable recordings were systematically obtained in all electrodes. Frequency analysis generated form the discrete Fourier transform (DFT) of signals recorded with carbon/ppEDOT, and pregelled electrodes illustrate similar frequency spectra, in accordance with the expected spectra for muscle activation.

Typical noise root mean square (RMS) levels were in the range of 83±20, 66±6 and 74±15 μV for carbon electrodes with a surface area of 20 mm$^2$, ppEDOT/carbon electrode array with a surface area of 20 mm$^2$ and commercially available pre-gelled electrodes with a surface area of 300 mm-, respectively. Noise RMS levels of the differential signals were in the range of 26±11 μV for uncoated electrode array, 25±9 μV for the ppEDOT electrode array and 22±9 μV for the commercially available electrodes. Owing to the high SNR, it was possible to record force sensitive data from the FDI at 0.2-0.5 N with a calibrated spring (FIG. 13B). Interestingly, e The linear correlation between the impedance and the inverse of electrode surface area was validated by testing electrodes at different sizes. To demonstrate the performances of the electrodes, two scenarios were considered: long-term recording from the FDI (FIGS. 13A and 13B), and from the zygomaticus major (ZM) muscle of the face (FIGS. 14A-G). Electrodes without ppEDOT were not sensitive enough to pick the 0.2 N.

Recording from the face was performed to highlight the true strength of the tattoo array. ZM, which pulls the corners of the mouth back and up into a smile, is particularly interesting for emotional expressions and bipolar subjective valence detection. The arrays were placed on the cheek, above the ZM (FIGS. 14A-C). A clear electrical response was observed while laughing and during a wide smile (FIGS. 14D and 14E), while a weaker response was measured during a sad expression (FIGS. 14F and 14G), demonstrating the capacity to differentiate between a smile (observed in the recordings using electrode Nos. 0-7 and electrode Nos. 3-4), and a sad expression (observed only in the recordings using electrode Nos. 0-7). Recordings from the face muscles were conducted on three individuals. The signals presented in FIGS. 14D-G are typical results obtained from the same person. Similar differentiation in response to different facial expressions was observed for both individuals.

In this Example, novel dry electrodes for long-term sEMG recordings according to some embodiments of the present invention were described. Small (down to 5 mm in diameter) electrodes allow high SNR recording without the need for a gel. This is an improvement from a long held view that asserted otherwise. In fact, many recent efforts to improve dry electrodes focused on skin penetration. The sEMG system described in this Example offers many benefits and uses. The electrodes are dry, avoiding the complications associated with electrolytic gel, such as skin irritation and gel drying that degrades long-term recordings. The spatial-resolution allows easy electrode placement that simplifies the recording procedure. The exact position of nerves and muscles is no longer a challenge, and can be achieved through different electrode configurations. The integration with electronic devices and wireless capabilities is easy and can be implemented with off-the-shelf electronics.

An advantage of the present embodiments is the use of screen-printing technology combined with a newly developed ppEDOT coating. Screen-printing is cheap and can be readily implemented in large-scale production. Moreover, different materials can be conveniently implemented to support the integration of chemical sensing. Another challenge addressed by the present embodiments is the need for low-temperature and dry surface modification process. ppEDOT was found to enhance the specific capacitance of the SPEs and contributed to a reduction in noise.

The preliminary safety studies presented in this Example reveal that ppEDOT electrodes cause no skin irritation and can be used for hours without discomfort. While focusing on sEMG, other bio-signals, such as EEG, can be collected using the electrodes of the present embodiments. By demonstrating sEMG recordings from the FDI and the face, the present Example revealed the potential of these electrodes for other applications.

Example 2

The device of the present embodiments can also record signals from rodents. Carbon nanotube based electrodes can be fabricated according to the layouts illustrated in FIGS. 15A-D. FIG. 15A shows the layout using 1 mm diameter electrodes, FIG. 15B shows the layout using 2 mm diameter electrodes, FIG. 15C shows the layout using 3 mm diameter electrodes, and FIG. 15D shows the layout superimposed on the head of a rodent.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Nieuwboer, A. et al. Electromyographic profiles of gait prior to onset of freezing episodes in patients with Parkinson's disease. Brain 127, 1650-1660, doi: 10.1093/brain/awh189 (2004).
2. Makeig, S. et al. Dynamic brain sources of visual evoked responses. Science 295, 690-694, doi: 10.1126/science.1066168 (2002).
3. Schafer, C., Rosenblum, M. G., Kurths, J. & Abel, H. H. Heartbeat synchronized with ventilation. Nature 392, 239-240, doi: 10.1038/32567 (1998).
4. Alilain, W. J., Horn, K. P., Hu, H., Dick, T. E. & Silver, J. Functional regeneration of respiratory pathways after spinal cord injury. Nature 475, 196-200, doi: 10.1038/nature10199 (2011).
5. Nicolelis, M. A. L. Actions from thoughts. Nature 409, 403-407, doi: 10.1038/35053191 (2001).
6. O'Doherty, J. E. et al. Active tactile exploration using a brain-machine-brain interface. Nature 479, 228-231, doi: 10.1038/nature10489 (2011).
7. Hardyck, C. D., Petrinov.Lf & Ellswort.Dw. Feedback of speech muscle activity during silent reading-rapid extinction. Science 154, 1467-1468, doi: 10.1126/science.154.3755.1467 (1966).
8. Zajonc, R. B. Emotion and facial efference: a theory reclaimed. Science 228, 15-21 (1985).
9. Larsen, J. T., Norris, C. J. & Cacioppo, J. T. Effects of positive and negative affect on electromyographic activity over zygomaticus major and corrugator supercilii. Psychophysiology 40, 776-785, doi: 10.1111/1469-8986.00078 (2003).
10. van Boxtel, A. In Proceedings of Measuring Behavior (eds A. J. Spink et al.) 104-108 (Eindhoven, The Netherlands, 2010).
11. Johnson, K. J., Waugh, C. E. & Fredrickson, B. L. Smile to see the forest: Facially expressed positive emotions broaden cognition. Cognition & Emotion 24, 299-321, doi: 10.1080/02699930903384667 (2010).
12. Searle, A. & Kirkup, L. A direct comparison of wet, dry and insulating bioelectric recording electrodes. Physiological Measurement 21, 271-283, doi: 10.1088/0967-3334/21/2/307 (2000).
13. McAdams, V. In Encyclopedia of medical devices and instrumentation (ed Webster J. G.) 120-166 (Wiley, 1988).
14. Bandodkar, A. J. et al. Tattoo-based potentiometric ion-selective sensors for epidermal pH monitoring. Analyst 138, 123-128, doi:10.1039/c2an36422k (2013).
15. Li, M., Li, Y. T., Li, D. W. & Long, Y. T. Recent developments and applications of screen-printed electrodes in environmental assays-A review. Analytica Chimica Acta 734, 31-44, doi: 10.1016/j.aca.2012.05.018 (2012).
16. Malzahn, K., Windmiller, J. R., Valdes-Ramirez, G., Schoning, M. J. & Wang, J. Wearable electrochemical sensors for in situ analysis in marine environments. Analyst 136, 2912-2917, doi: 10.1039/clan15193b (2011).
17. Bareket, L., Rephaeli, A., Berkovitch, G., Nudelman, A. & Rishpon, J. Carbon nanotubes based electrochemical biosensor for detection of formaldehyde released from a cancer cell line treated with formaldehyde-releasing anti-cancer prodrugs. Bioelectrochemistry 77, 94-99, doi: 10.1016/j.bioelechem.2009.06.016 (2010).

18. Lepola, P. et al. Screen-printed EEG electrode set for emergency use. Sensors and Actuators a-Physical 213, 19-26, doi: 10.1016/j. sna.2014.03.029 (2014).
19. Webb, R. C. et al. Ultrathin conformal devices for precise and continuous thermal characterization of human skin. Nature Materials 12, 938-944, doi: 10.1038/nmat3755 (2013).
20. Kim, D. H. et al. Epidermal Electronics. Science 333, 838-843, doi: 10.1126/science.1206157 (2011).
21. Leleux, P. et al. Organic Electrochemical Transistors for Clinical Applications. Advanced Healthcare Materials 4, doi: 10.1002/adhm.201400356 (2015).
22. Huigen, E., Peper, A. & Grimbergen, C. A. Investigation into the origin of the noise of surface electrodes. Medical & Biological Engineering & Computing 40, 332-338, doi: 10.1007/bf02344216 (2002).
23. Bareket, L. et al. Semiconductor Nanorod-Carbon Nanotube Biomimetic Films for Wire-Free Photostimulation of Blind Retinas. Nano Letters 14, 6685-6692, doi: 10.1021/nl5034304 (2014).
24. Zou, L. et al. Surface hydrophilic modification of RO membranes by plasma polymerization for low organic fouling. Journal of Membrane Science 369, 420-428, doi: 10.1016/j.memsci.2010.12.023 (2011).
25. Khodagholy, D. et al. NeuroGrid: recording action potentials from the surface of the brain. Nature Neuroscience 18, 310-315, doi:10.1038/nn.3905 (2015).
26. Gerwig, R. et al. PEDOT-CNT Composite Microelectrodes for Recording and Electrostimulation Applications: Fabrication, Morphology, and Electrical Properties. Frontiers in Neuroengineering 5, 8, doi: 10.3389/fneng.2012.00008 (2012).
27. Yasuda, H. Glow-discharge polymerization. Macromolecular Reviews Part D-Journal of Polymer Science 16, 199-293 (1981).
28. Gong, X. Y., Dai, L. M., Mau, A. W. H. & Griesser, H. J. Plasma-polymerized polyaniline films: Synthesis and characterization. Journal of Polymer Science Part a-Polymer Chemistry 36, 633-643 (1998).
29. David-Pur, M., Bareket-Keren, L., Beit-Yaakov, G., Raz-Prag, D. & Hanein, Y. All-carbon-nanotube flexible multi-electrode array for neuronal recording and stimulation. Biomedical Microdevices 16, 43-53, doi: 10.1007/s10544-013-9804-6 (2014).
30. Griss, P., Tolvanen-Laakso, H. K., Merilainen, P. & Stemme, G. Characterization of micromachined spiked biopotential electrodes. IEEE Transactions on Biomedical Engineering 49, 597-604, doi: 10.1109/tbme.2002.1001974 (2002).

What is claimed is:

1. A method of measuring signals from a surface, the method comprising:
    placing on the surface a sensing device having an array of dry electrodes screen-printed on a double sided adhesive film, without use of impedance matching medium or gel between said electrodes and the surface, such that the electrodes conform with the shape of the surface and there is a direct contact between the electrodes and the surface; and
    collecting signals from said sensing device;
    wherein said dry screen-printed electrodes comprise conductive carbon ink, wherein said electrodes are on one side of said film and said surface is attached to an opposite side of said film, and wherein said film comprises a plurality of openings to expose a sensing portion of each electrode to the surface.

2. The method according to claim 1, wherein said collecting is executed continuously or intermittently over a time period of at least a few hours without detaching said sensing device from the surface.

3. The method according to claim 1, wherein said collecting is executed continuously or intermittently over a time period of at least a few hours while a signal to noise ratio of said signals is not reduced by more than 10%.

4. The method according to claim 1, wherein said signals are EMG signals.

5. The method according to claim 1, wherein said signals are EEG signals.

6. The method according to claim 1, wherein said signals are ECG signals.

7. The method according to claim 1, wherein said signals are EOG signals.

8. The method according to claim 1, wherein said surface is selected from the group consisting of a surface of a biological material, a surface of a natural tissue, a surface of an ex-vivo natural tissue, a surface of an in-vivo natural tissue, a surface of an artificial tissue, a surface of an ex-vivo artificial tissue, a surface of an in-vivo artificial tissue, a skin of a subject, a surface of an internal organ of a subject, a surface of a cell culture.

9. The method according to claim 1, being employed for sleep analysis.

* * * * *